(12) United States Patent
Mandelis et al.

(10) Patent No.: US 8,649,835 B2
(45) Date of Patent: Feb. 11, 2014

(54) METHOD OF PERFORMING WAVELENGTH MODULATED DIFFERENTIAL LASER PHOTOTHERMAL RADIOMETRY WITH HIGH SENSITIVITY

(76) Inventors: Andreas Mandelis, Scarborough (CA); Xinxin Guo, Toronto (CA)

( * ) Notice: Subject to any disclaimer, the term of this patent is extended or adjusted under 35 U.S.C. 154(b) by 481 days.

(21) Appl. No.: 12/948,525

(22) Filed: Nov. 17, 2010

(65) Prior Publication Data

US 2011/0118571 A1  May 19, 2011

Related U.S. Application Data

(60) Provisional application No. 61/261,929, filed on Nov. 17, 2009.

(51) Int. Cl.
*A61B 5/1455* (2006.01)

(52) U.S. Cl.
USPC .......................................... 600/316; 600/310

(58) Field of Classification Search
USPC .................. 600/310, 316, 322; 250/252.1
See application file for complete search history.

(56) References Cited

U.S. PATENT DOCUMENTS

| | | | |
|---|---|---|---|
| 5,377,006 A * | 12/1994 | Nakata | 356/486 |
| 5,553,616 A | 9/1996 | Ham et al. | |
| 5,896,198 A | 4/1999 | Chou et al. | |
| 6,002,953 A * | 12/1999 | Block | 600/316 |
| 6,044,285 A * | 3/2000 | Chaiken et al. | 600/316 |
| 6,580,934 B1 * | 6/2003 | Braig et al. | 600/310 |
| 6,709,857 B2 | 3/2004 | Bachur, Jr. | |
| 7,729,734 B2 | 6/2010 | Mandelis et al. | |
| 2004/0135085 A1 | 7/2004 | Trofimov et al. | |
| 2004/0225206 A1 | 11/2004 | Kouchnir | |
| 2005/0137469 A1 | 6/2005 | Berman et al. | |

* cited by examiner

*Primary Examiner* — Eric Winakur
(74) *Attorney, Agent, or Firm* — Lynn C. Schumacher; Stephen W. Leonard; Hill & Schumacher

(57) ABSTRACT

Methods are provided for the detection of an analyte in a sample using wavelength modulated differential photothermal radiometry with enhanced sensitivity. A wavelength modulated differential photothermal radiometry system, comprising two optical modulated beams, where each beam experiences different absorption by the analyte, is calibrated by controlling the relative phase difference between the modulated beams so that individual photothermal signals corresponding to each modulated beam are 180° out of phase, corresponding to peak sensitivity to analyte concentration. The system may be further calibrated by varying the relative intensities of the two modulated beams and measuring standards containing known analyte concentration in order to determine an optimal relative intensity for a given concentration range of interest.

26 Claims, 21 Drawing Sheets

METHOD OF PERFORMING WAVELENGTH MODULATED DIFFERENTIAL LASER PHOTOTHERMAL RADIOMETRY WITH HIGH SENSITIVITY

CROSS-REFERENCE TO RELATED APPLICATION

This application claims priority to U.S. Provisional Application No. 61/261,929, titled "METHOD OF PERFORMING WAVELENGTH MODULATED DIFFERENTIAL LASER PHOTOTHERMAL RADIOMETRY WITH HIGH SENSITIVITY" and filed on Nov. 17, 2009, the entire contents of which are incorporated herein by reference.

FIELD OF THE INVENTION

This invention relates to the detection of a material via its optical and thermal properties. More particularly, the present invention relates to the non-invasive detection of glucose.

BACKGROUND OF THE INVENTION

It is now well recognized that the world is in the midst of a global epidemic of diabetes. Diabetes has become one of the leading causes of death and disability in the world (1). Patients can be at serious risk depending on the concentration and duration of blood glucose values: low levels (hypoglycaemia) for any length of time are associated with acute danger (brain damage, even death), while high levels (hyperglycaemia) have a chronic impact over days or years including heart and kidney failure, blindness and amputations (2).

For proper diabetes management, frequent monitoring of blood glucose is required (3). The current standard technique for self-monitoring of blood glucose requires a skin puncture to draw a small blood sample. However, the discomfort and pain of the procedure lead to poor compliance. Quick, reliable and pain-free testing are three highly desirable characteristics for patients.

Over the past two decades the pursuit of non-invasive methods of glucose monitoring has resulted in the development of a number of optical technologies (4,5). The near infrared (NIR) spectral range has been well explored because of the relatively low water absorption (4,6). However, the NIR glucose absorption bands are weak (overtone and combination bands) and overlapped with other blood constituents. Separation often requires sophisticated processing algorithms.

In comparison, the middle infrared (MIR) region is extremely useful for glucose identification. Of particular significance is the prominent absorption peak in the 8.5-10.5 µm band which is due to the carbon-oxygen-carbon bond in the pyran ring of glucose. This feature is peaked at ca. 9.7 µm, and is isolated from other interfering peaks in human blood (7-12). A major difficulty in the MIR is the intrinsic high-background absorption coefficient of water which tends to fully dominate the relatively low absorption of normal glucose concentration in human blood.

Recently, a new approach to the non-invasive detection of glucose was disclosed in US Patent Application Publication No. US20070213607. This new method, which is henceforth referred to as wavelength modulated differential photothermal radiometry (WM-DPTR), involves the measurement of glucose in a sample by the differential detection of a thermal emission produced by two incident optical beams. The differential detection is achieved by modulating the intensity of the two beams 180° out of phase, and selecting the wavelengths of the two beams to be on and off of the glucose absorption peak near a wavelength near 9.7 µm.

While this method has specifically been shown to successfully detect glucose with a sensitivity superior to other optical methods, it is desirable to further improve the sensitivity of the method. It would also be advantageous to adapt the method to the measurements of other types of samples.

SUMMARY OF THE INVENTION

Embodiments of the present invention provide a major improvement over the initial WM-DPTR method, achieving a dramatic improvement in sensitivity, and further enabling the method to be applied to a wide class of materials. Specifically, embodiments disclosed herein provide a method of calibrating a wavelength modulated differential photothermal radiometry system in which the relative intensity and/or the relative phase, of the two photothermal signals, are controlled. The sensitivity may also be tailored to a specific measurement range by controlling the relative intensity and phase of the two photothermal signals to obtain improved sensitivity over the specific measurement range.

Accordingly, in a first aspect, there is provided a method of calibrating a wavelength modulated differential photothermal radiometry system for detecting the presence of an analyte within a substance, the method comprising the steps of: providing a first optical beam and a second optical beam, wherein the first optical beam is characterized by a first wavelength and the second optical beam is characterized by a second wavelength, and wherein the first wavelength is selected so that analyte concentrations within a concentration range of interest will cause sufficient absorption of the first optical beam to produce detectable thermal-wave emission, and wherein an absorption coefficient of the analyte at the first wavelength exceeds that at the second wavelength; producing a first modulated beam and a second modulated beam by modulating an intensity of the first optical beam and an intensity of the second optical beam, respectively; wherein the first modulated beam and the second modulated beam are modulated at a substantially equal modulation frequency, and wherein a phase difference between the first modulated beam and the second modulated beam is approximately 180 degrees; providing a reference sample substantially free of analyte; directing and substantially overlapping the first modulated beam and the second modulated beams onto the reference sample; measuring a first photothermal signal produced by the first modulated beam; measuring a second photothermal signal produced by the second modulated beam; obtaining a relative photothermal phase between the first photothermal signal and the second photothermal signal; and controlling a relative phase of the first modulated beam and the second modulated beam so that the relative photothermal phase is approximately 180 degrees. The relative intensity is preferably controlled by varying an intensity of the second modulated beam.

The method preferably further comprises the steps of: measuring a differential photothermal signal for one or more standards, each the standard comprising a known analyte concentration, while controlling a relative intensity of the first modulated beam and the second modulated beam to scan a photothermal amplitude ratio of the first photothermal signal and the second photothermal signal near unity; and selecting the photothermal amplitude ratio corresponding to a desired sensitivity over the concentration range of interest. Calibration data is preferably generated for the photothermal amplitude ratio corresponding to the desired sensitivity over the concentration range of interest.

The method may further comprise measuring an unknown sample comprising an unknown analyte concentration within the substance, and determining the unknown analyte concentration by relating a differential photothermal signal obtained when measuring the unknown sample to the calibration data.

Prior to the step of controlling the relative phase, a relative intensity of the first modulated beam and the second modulated beam is preferably controlled so that a ratio of the first photothermal signal amplitude and the second photothermal signal amplitude is approximately unity.

A relative intensity of the first modulated beam and the second modulated beam is preferably controlled to scan a relative photothermal amplitude of the first photothermal signal and the second photothermal signal near unity; the method further comprising measuring the first photothermal signal and the second photothermal signal; and verifying that the relative photothermal phase is substantially 180 degrees.

The first optical beam is preferably provided by a first laser, and the second modulated beam is preferably provided by a second laser, wherein the photothermal amplitude ratio may be controlled by varying a voltage or current of one of more of the first and second lasers. The relative phase is preferably controlled by varying a phase difference between modulation voltages or currents of the first laser and the second laser.

Prior to the step of controlling the relative phase, an intensity of the first modulated beam is preferably controlled so that an amplitude of first photothermal signal is approximately half of a full-scale amplitude range corresponding to the concentration range of interest.

The substance is preferably tissue and the analyte is preferably glucose.

The method may further comprise the step of: measuring a differential photothermal signal for one or more standards, each the standard comprising a known analyte concentration, while controlling a relative intensity of the first modulated beam and the second modulated beam to scan a relative photothermal amplitude of the first photothermal signal and the second photothermal signal near unity; and determining calibration data based on a relationship between each known analyte concentration and a relative intensity at which a phase flip-over occurs. An unknown sample may then be measured comprising an unknown analyte concentration within the substance, wherein the unknown analyte concentration is determined by relating a relative intensity at which phase flip-over occurs when measuring the unknown sample to the calibration data.

In another aspect, there is provided a method of calibrating a wavelength modulated differential photothermal radiometry system for detecting the presence of an analyte within a substance, the method comprising the steps of: providing a first optical beam and a second optical beam, wherein the first optical beam is characterized by a first wavelength and the second optical beam is characterized by a second wavelength, and wherein the first wavelength is selected so that analyte concentrations within a concentration range of interest will cause sufficient absorption of the first optical beam to produce detectable thermal-wave emission, and wherein an absorption coefficient of the analyte at the first wavelength exceeds that at the second wavelength; producing a first modulated beam and a second modulated beam by modulating an intensity of the first optical beam and an intensity of the second optical beam, respectively; wherein the first modulated beam and the second modulated beam are modulated at a substantially equal modulation frequency, and wherein a phase difference between the first modulated beam and the second modulated beam is approximately 180 degrees; providing a reference sample comprising a known concentration of analyte; directing and substantially overlapping the first modulated beam and the second modulated beams onto the reference sample; obtaining a differential photothermal signal by detecting emission radiated by the reference sample with a phase-sensitive detection system; and varying an intensity ratio of the first modulated beam and the second modulated beam to minimize the differential photothermal signal.

The known concentration of analyte is preferably approximately zero. The substance is preferably tissue and the analyte is preferably glucose.

Calibration data is preferably obtained by relating signals obtained from standard samples with known analyte concentrations to the known analyte concentrations. An unknown sample comprising an unknown analyte concentration within the substance may then be measured, and the unknown analyte concentration may be determined by relating a differential photothermal signal obtained when measuring the unknown sample to the calibration data.

The intensity ratio may be varied by controlling one or more of a spatial overlap and a relative spatial size of the first modulated beam and the second modulated beam, and is preferably varied by controlling a diameter of an iris placed in a path of one of the first modulated beam and the second modulated beam.

The step of obtaining a signal by detecting emission radiated by the reference sample with a phase-sensitive detection system preferably comprises the steps of: collecting the emission radiated by the reference sample; directing the emission onto a detector, wherein the detector is adapted to produce a signal related to the emission; providing the signal and a reference signal to a lock-in amplifier, thereby obtaining a phase-sensitive differential photothermal signal. Collected power having a wavelength corresponding to the first modulated beam and the second modulated beam is preferably spectrally filtered.

In yet another embodiment, there is provided a method of calibrating a wavelength modulated differential photothermal radiometry system for detecting the presence of an analyte within a substance, the method comprising the steps of: a) providing a first optical beam and a second optical beam, wherein the first optical beam is characterized by a first wavelength and the second optical beam is characterized by a second wavelength, and wherein the first wavelength is selected so that analyte concentrations within a concentration range of interest will cause sufficient absorption of the first optical beam to produce detectable thermal-wave emission, and wherein an absorption coefficient of the analyte at the first wavelength exceeds that at the second wavelength; b) producing a first modulated beam and a second modulated beam by modulating an intensity of the first optical beam and an intensity of the second optical beam, respectively; wherein the first modulated beam and the second modulated beam are modulated at a substantially equal modulation frequency, and wherein a phase difference between the first modulated beam and the second modulated beam is approximately 180 degrees; c) selecting an intensity ratio of the first modulated beam and the second modulated beam; d) providing a reference sample comprising a known concentration of analyte; e) directing and substantially overlapping the first modulated beam and the second modulated beams onto the reference sample; f) obtaining a differential photothermal signal by detecting emission radiated by the reference sample with a phase-sensitive detection system; g) repeating steps d) to f) one or more times to measure differential photothermal signals for one or more additional standard samples, wherein each the additional standard samples comprise different known analyte concentrations; h) obtaining a calibration curve by relating the differential photothermal signals to the known analyte concentrations; i) repeating steps c) to h) to obtain an additional calibration curve corresponding to a different intensity ratio; and j) selecting a preferred calibration curve having a desired sensitivity over a predetermined range of analyte concentration, and placing the system into a configuration corresponding to the preferred calibration curve.

Step i) is preferably repeated one or more times prior to performing step j).

The substance is preferably tissue and the analyte is preferably glucose.

An unknown sample comprising an unknown analyte concentration within the substance may then be measured, and the unknown analyte concentration may be determined by relating a signal obtained when measuring the unknown sample to the preferred calibration curve.

In still another embodiment, there is provided an apparatus for performing wavelength modulated differential photothermal radiometry for detecting the presence of an analyte within a substance, the apparatus comprising: a first optical source and a second optical source, wherein the first optical source is characterized by a first wavelength and the second optical source is characterized by a second wavelength, and wherein the first wavelength is selected so that analyte concentrations within a concentration range of interest will cause sufficient absorption of the first optical source to produce detectable thermal-wave emission, and wherein an absorption coefficient of the analyte at the first wavelength exceeds that at the second wavelength; modulation means for producing a first modulated beam and a second modulated beam by modulating an intensity of the first optical source and an intensity of the second optical source, respectively, wherein the modulation means is configured to modulate the first modulated beam and the second modulated beam at a substantially equal modulation frequency, phase control means for controlling a relative phase between the first modulated beam the second modulated beam; intensity control means for controlling a relative intensity of the first modulated beam and the second modulated beam; optical means for directing and spatially overlapping the first modulated beam and the second modulated beam onto a sample; collection means for collecting photothermal radiation emitted from the sample; a phase-sensitive detector for obtaining a signal related to the photothermal radiation.

The first optical source and the second optical source are preferably a first laser and a second laser, respectively, wherein the modulation means comprises a first electrical waveform and a second electrical waveform for driving the first laser and the second laser, respectively, and wherein the phase control means comprises an electrical controller for varying a phase difference between the first electrical waveform and the second electrical waveform.

A further understanding of the functional and advantageous aspects of the invention can be realized by reference to the following detailed description and drawings.

BRIEF DESCRIPTION OF THE DRAWINGS

The embodiments of the present invention are described with reference to the attached figures, wherein.

DETAILED DESCRIPTION OF THE INVENTION

Generally speaking, the systems described herein are directed to a method of performing wavelength modulated differential laser photothermal radiometry with high sensitivity. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a method of performing wavelength modulated differential laser photothermal radiometry with high sensitivity for the detection of glucose.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately, when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the expression $P_A$-$P_B$ refers to the phase difference between the individual photothermal signals (typically measured from a reference), the expression $P_{AB}$ refers to the differential phase (typically measured for a sample), $\Delta P_{AB}$ refers to the differential phase change (typically shown for samples), $A_{AB}$ refers to the differential photothermal amplitude (typically measured for samples), R=$A_A$/$A_B$ refers to the ratio of differential photothermal amplitudes of the two individual beams (typically measured for a reference), and $I_R$=$I_A$/$I_B$ refers to the laser intensity ratio.

Figure 1:
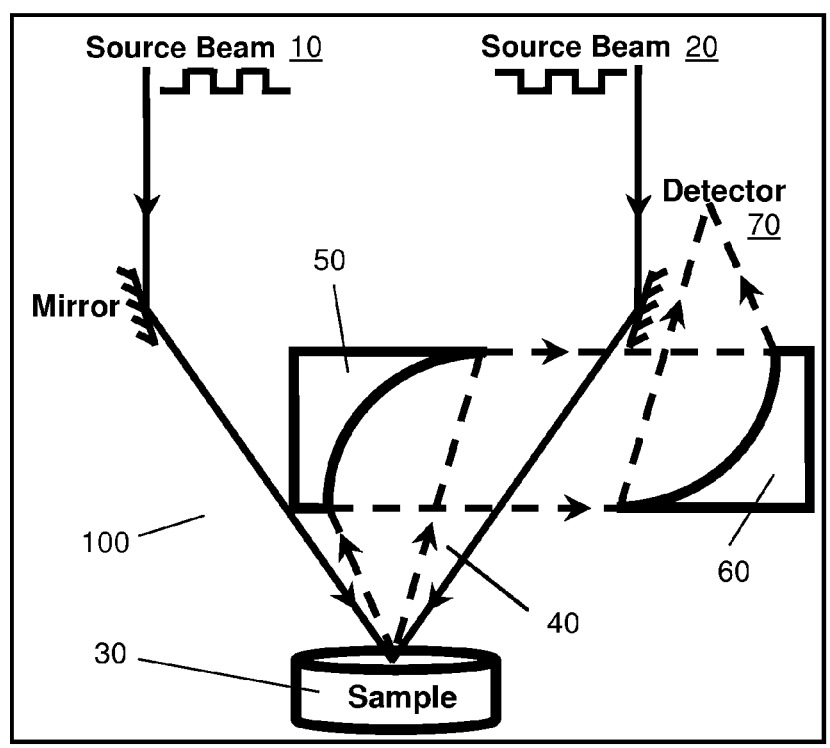
FIG. 1 shows a schematic of the WM-DPTR system according to the prior art.

Embodiments of the present invention provide apparatus and methods for performing wavelength-modulated differential photothermal radiometry (WM-DPTR), where the apparatus may be calibrated for improved sensitivity. Prior to describing the embodiments, it is useful to review known methods of performing WM-DPTR. Referring to FIG. 1, an apparatus 100 for performing the WM-DPTR method is shown, in which a first optical beam 10 and a second optical beam 20 are directed onto and spatially overlapped on the surface of a sample 30 that may contain glucose. This system was taught in U.S. Pat. No. 7,729,734, titled "Non-invasive Biothermophotonic Sensor for Blood Glucose Monitoring", and filed on Mar. 7, 2006, which is incorporated herein in its entirety.

Figure 2:
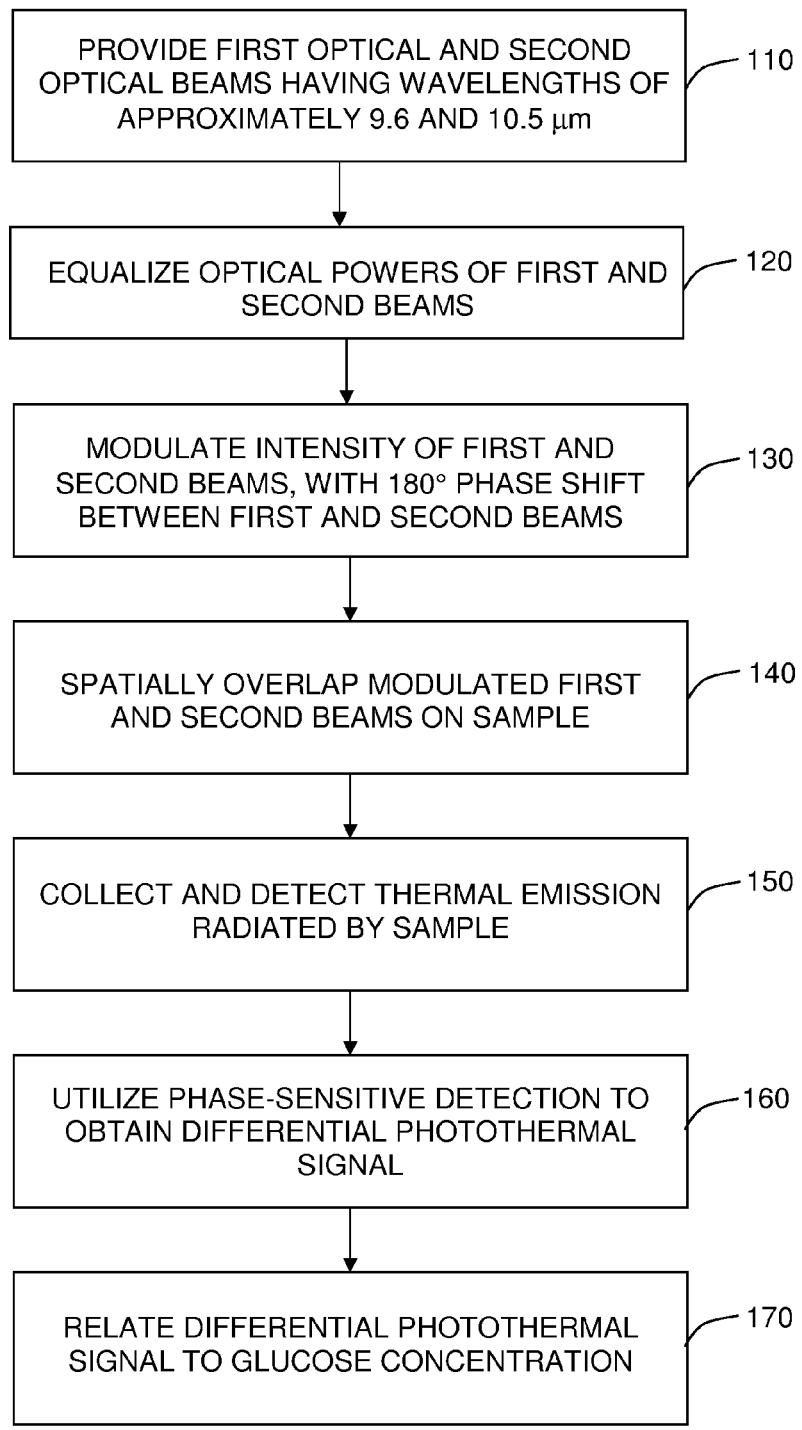
FIG. 2 shows a flow chart describing the WM-DPTR method as taught in the prior art.

FIG. 2 provides a flow chart illustrating the aforementioned method, in which a key requirement was the prescription that the intensities of the two source beams be equalized. In Step 110, two optical beams are provided, where the wavelength of the first beam is selected to be near the mid-IR glucose peak at a wavelength of approximately 9.6 μm, and the wavelength of the second beam is selected to be adjacent to the peak, preferably close to a wavelength of approximately 10.5 µm. In step 120, the intensities (or optical power) of both beams are equalized.

The intensity of both beams is modulated in step 130, with modulation of the first beam being 180° relative to that of the second beam, and the beams are spatially overlapped on the sample in step 140. The wavelength modulation arrangement gives rise to destructive interference over one modulation period between the two thermal waves generated through optical absorption at the two chosen wavelengths at the peak and trough (baseline) of the glucose absorption band. The destructive interference causes the generation of a differential thermal-wave signal within the tissue sample that is emitted with a modulated form having the common frequency of the source modulation. The emission 40 is collected in step 150 using mirrors 50 and 60 and measured with a broadband detector 70. The detector bandwidth is selected to exclude the detection of the source beams, either by selecting a detector with the appropriate internal spectral bandwidth, or by externally filtering the optical signal incident on the detector. Lock-in detection is employed to extract a signal in step 160, and the signal is employed to estimate the glucose concentration in step 170.

As disclosed in the embodiments below, the present inventors have made the discovery that the sensitivity of the WM-DPTR method can be significantly improved according to calibration procedure in which the amplitude, and preferably the phase, of the individual photothermal signals, is controlled. The additional calibration steps provide the control required to tailor the relative generation of thermal waves by the two beams, and to obtain a differential signal with improved sensitivity and signal to noise ratio.

Figure 3:
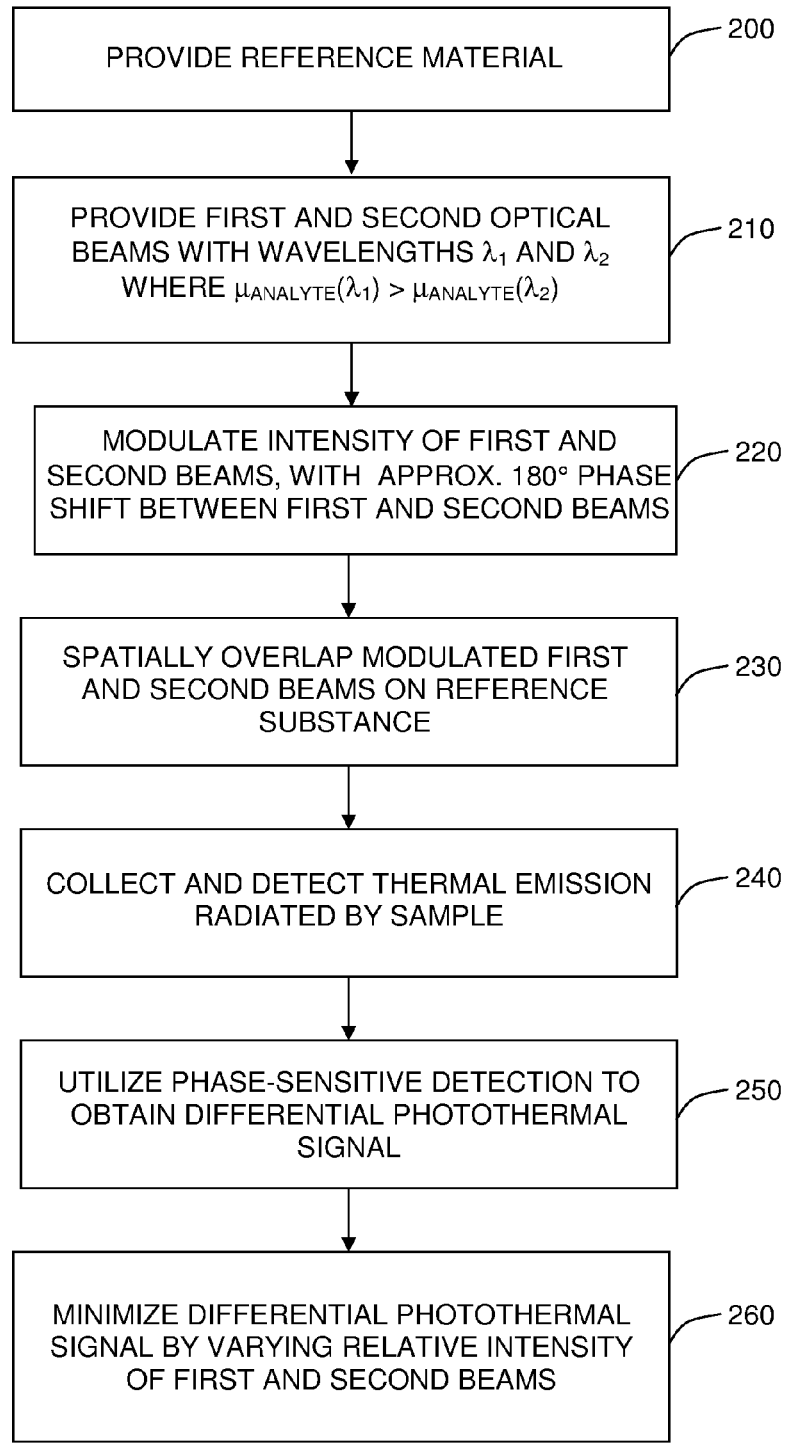
FIG. 3 shows a flow chart describing the modified WM-DPTR method according to an embodiment of the present invention.

FIG. 3 provides a flow chart illustrating an embodiment for calibrating a WM-DPTR system for the subsequent determination of the presence or concentration of an analyte within a substance. In step 200, a reference material is provided for performing the calibration. The reference material is preferably free of analyte, in which case the absorption spectrum of the reference material is a background absorption spectrum. Non-limiting examples of reference materials are water and blood products such as serum, whole blood and synthetic blood.

The wavelengths of the optical beams are selected in step 210. The wavelength of the first beam is selected to correspond to a wavelength at which optical radiation will be absorbed by the analyte. Preferably, the wavelength of the first beam is selected so that analyte concentrations within a concentration range of interest will cause sufficient absorption of the beam to produce detectable thermal-wave emission. The wavelength of the second beam is then selected by requiring that the absorption of the first beam by the analyte exceeds that of the second beam (i.e. the absorption coefficient of the analyte at the first wavelength exceeds that at the second wavelength).

Preferably, the wavelength of the first beam is tuned to a spectral region where the presence of the analyte causes substantial absorption, such as a peak in the absorption spectrum of the analyte. The wavelength of the second beam is preferably tuned to a minimum or off-peak spectral location. A larger difference between the absorption coefficients at the first and second wavelengths will produce a correspondingly larger differential signal. Unlike previously known methods of WM-DPTR, the background absorption coefficient (i.e. the absorption coefficient of the reference) need not be equal at the first and second wavelengths. Preferably, the difference between the absorption coefficients of the reference material at the first and second wavelengths is low compared to difference between the absorption coefficients of the analyte alone at the first and second wavelengths, for at least a portion of the analyte concentrations of interest. More preferably, the absorption coefficients of the reference material at the first and second wavelengths are within an order of magnitude for at least a portion of the analyte concentrations of interest.

While the first and second beams are described as having first and second wavelengths, respectively, those skilled in the art will appreciate that the first and/or second beam may comprise a range of wavelengths. In such a case, the wavelength as discussed above could be the average wavelength, median wavelength, or any other statistically relevant measure of a characteristic wavelength. Furthermore, the first and second beams may comprise incoherent sources or coherent sources. Preferably, the first and second sources have lateral intensity profiles that are highly symmetric and free of hotspots.

In step 220, the first and second beams are modulated in intensity with a phase difference of 180°, and spatially overlapped on the sample in step 230, as noted above. The photothermal emission is collected in step 240, and a photothermal signal is detected using a phase-sensitive detection system in step 250. The phase-sensitive detection system preferably comprises a lock-in amplifier, which is provided with a reference signal related to the intensity modulation frequency and phase.

In step 260, the sensitivity of the system is enhanced through a central step in the calibration method that involves varying the relative intensity of the two beams. The sensitivity is enhanced by decreasing the detected differential signal while varying the relative intensity ratio of the two beams. Preferably, the differential signal is minimized.

The minimum signal represents a configuration in which the contribution to the thermal-wave emission differential signal from the reference substance has been minimized, which serves to provide an improved signal-to-noise ratio when subsequently measuring samples with an unknown analyte concentration within the substance. Preferably, a standard calibration curve is obtained prior to measuring unknown samples (where the samples each comprise an unknown concentration of analyte within the substance), by relating the differential signals obtained from measuring standard samples with known concentrations of analyte within the substance.

The control of the relative intensity of the beams at the sample surface may be achieved by controlling any one or more of the following: intensity, optical power, spatial beam profile, spatial beam quality, and relative spatial overlap of the beams. Suitable means for achieving this control include, but are not limited to, one or more irises, polarized sources with waveplates, variable-angle beamsplitters, beam steering mirrors, spatial filters, telescopes, neutral density filters, and direct control of the laser intensity (for example, by controlling the laser voltage or current). In one embodiment, first and second irises are provided in the first and second beam paths, respectively. More preferably, at least one of the first and second irises is controllable by a control means such as a motor and a computer.

As is clearly shown in FIG. 3, the new calibration method is not limited to the glucose-tissue system, and can be adapted to a wide range of applications and material systems, including systems with overlapping background absorption features of absorption coefficients higher or much higher than the analyte or material system, which, however, remain fixed with changes in the absorption coefficient of the analyte, for example, due to concentration changes.

In another preferred embodiment, a method of calibrating a WM-DPTR system is provided in which multiple calibration curves are obtained for different configurations of the system, and the configuration corresponding to the calibration curve with the desired sensitivity over a selected range of analyte concentration is used in subsequent measurements of unknown samples.

The method first involves performing the WM-DPTR method on a series of standard (i.e. calibration) samples, each comprising a substance with a known concentration of analyte. After having obtained a first calibration curve, obtained from the relationship between the measured differential signals and the known analyte concentrations, the configuration of the system is modified by varying the intensity ratio of the first and second beams, using, for example, any of the methods listed above. This modification changes the calibration curve, and the new calibration curve is measured. This process may be repeated to obtain a set of calibration curves, each corresponding to different configurations of the system.

After having obtained at least two calibration curves, a preferred calibration curve is selected from the set of measured calibration curves by choosing the calibration curve with the desired sensitivity (or dynamic range) over a predetermined range of analyte concentrations. The system is then placed in the configuration corresponding to the preferred calibration curve. Preferably, a given system configuration may be recorded and/or reproduced, so that it may be re-established at a later point in time. This can be achieved, for example, by using an actuating means providing angular and/or positional feedback. For example, the radius of an iris used to control the relative spatial overlap of the beams may be varied using a stepper motor controlled by a computer.

In a variation on the aforementioned embodiment, more than one preferred calibration curve can be selected for use when measuring a sample comprising an unknown analyte concentration in the substance. For example, an initial measurement may be made using a system configuration having low sensitivity, but a high dynamic range over a broad analyte concentration range. After determining an estimate of the analyte concentration, a more accurate measurement can be obtained by modifying the system configuration to correspond to a calibration curve with higher sensitivity near the approximate concentration, and re-measuring the sample to obtain an improved determination of the analyte concentration. In another embodiment, a sample may be measured in multiple system configurations, with each configuration having a narrow dynamic range and high sensitivity over a specific analyte concentration range. The configuration for which the analyte concentration could be determined with the best sensitivity would be used to estimate the analyte concentration.

The sensitivity to the relative beam intensity was an unexpected discovery that can be understood through analysis of the mechanisms behind the thermal generation underlying the WM-DPTR method. The WM-DPTR method is not only based on the optical and thermal property changes acting independently, but also on the interdependence of these properties which enhances differential signals: The thermal effusivity change acts as an amplifying factor of the optical absorption coefficient change. This is very important as optical changes add chromophore selectivity to WM-DPTR, whereas thermal changes alone cannot.

Figure 4:
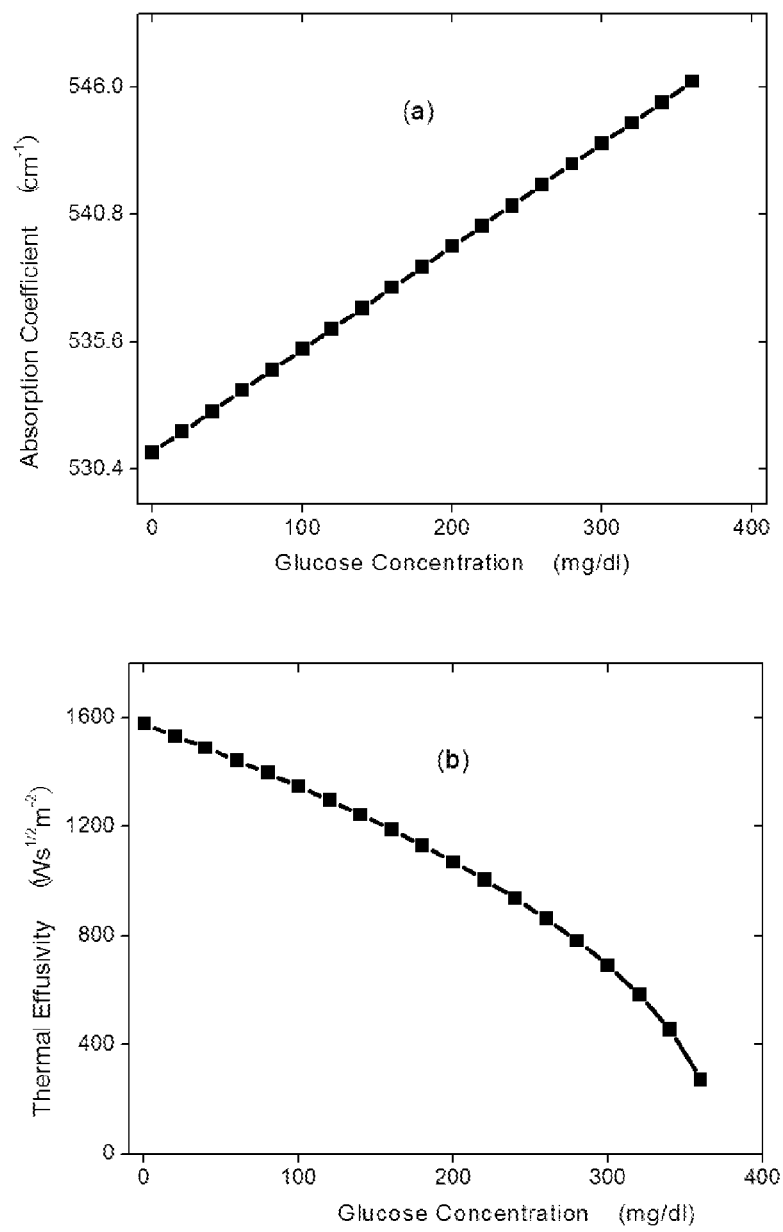
FIG. 4 shows the dependence of thermal and optical properties of aqueous glucose solutions in 0-400 mg/dl range; (a) absorption coefficient vs. glucose concentration. (b) thermal effusivity vs. glucose concentration

For example, the absorption coefficient and thermal effusivity of glucose, is shown in FIG. 4. As shown in the figure, a 360 mg/dl change in glucose concentration results in ~83% change in thermal effusivity and ~2.8% change in optical absorption coefficient, both contributing to ~170% change in the WM-DPTR signal.

The cross-enhancement or amplification of the WM-DPTR signal resulting from the optical and thermal interdependence in the presence of analyte in a background material can be physically understood as follows: At each excitation wavelength $\lambda_A$ and $\lambda_B$ (corresponding to the first and second sources), a change in analyte concentration changes the optical absorption depth $1/\mu_{aA}$ ($1/\mu_{aB}$ remains unchanged). The resulting optical absorption and non-radiative conversion at the two wavelengths then generates proportional changes in thermal distributions depthwise in the material (they shift the photothermal-wave centroid with changing $\mu_{aA}$. The heat conducted away from the surface and subsurface locations in the (substance+analyte) mixture or material does so at a rate strongly dependent on the thermal properties (effusivity and diffusivity). These properties also change with analyte concentration and this fact acts as an amplifying factor of the optical asymmetry at $\lambda_A$ and $\lambda_B$ with changing analyte concentration.

To illustrate the sensitivity of the WM-DPTR to relative beam intensity, the glucose-in-water system was selected and modeled theoretically. A theoretical analysis of the WM-DPTR signal generation in tissue was developed using a 1-D heat conduction equation in the frequency domain, with a harmonic laser-induced heat source at subsurface depth z of tissue following optical absorption at wavelength $\lambda_{IR}$ ($\lambda_A$ or $\lambda_B$ in our case) with absorption coefficient $\mu_a(\lambda_{IR})$ ($\mu_{aA}$ or $\mu_{aB}$ in our case). The resulting IR radiometric flux (signal) can be written as $$\tilde{S}(\omega) = \frac{I_0}{\kappa} \int_{\lambda_{ir1}}^{\lambda_{ir2}} \left[ \frac{\partial M(\lambda_{ir}, T_0)}{\partial T} \right] \quad (1)$$

$$\frac{\mu_{ir}\mu_a(\lambda_{IR})}{(\sigma^2 - \mu_a(\lambda_{IR})^2)} \left[ \frac{1}{\mu_a(\lambda_{IR}) + \mu_{ir}} - \left[ \frac{\kappa\mu_a(\lambda_{IR}) + h}{\kappa\sigma + h} \right] \frac{1}{\sigma + \mu_{ir}} \right] d\lambda_{ir}$$

where $M(\lambda_{ir}, T_o)$ is the Planck distribution function at the ambient temperature $T_0$, $\kappa$ is the thermal conductivity of tissue, $I_0$ (W/cm$^2$) is the laser intensity, $\omega$ is the angular frequency of modulation $\sigma(\omega)=\sqrt{i\omega/D}$ is the complex thermal wave number; D is the thermal diffusivity and h is the heat loss coefficient. $\lambda_{ir}$ and $\mu_{ir}$ are emission wavelength and absorption coefficient of the tissue. $\lambda_{ir1}$-$\lambda_{ir2}$ is the detector bandwidth.

For the WM-DPTR system, excitation wavelengths $\lambda_A$=9.5 μm, $\lambda_B$=10.4 μm, the absorption coefficients at the two excitation wavelengths are $\mu_{aA}$ (glucose dependent) and $\mu_{aB}$ (glucose independent). The emission wavelength range is confined within the simulated spectral bandwidth of a MCZT thermal detector: 2-5 μm. Thermal effusivity e (glucose dependent) is related to thermal conductivity $\kappa$ and thermal diffusivity D in Eq. (1) through $e=\kappa/\sqrt{D}$.

Figure 5:
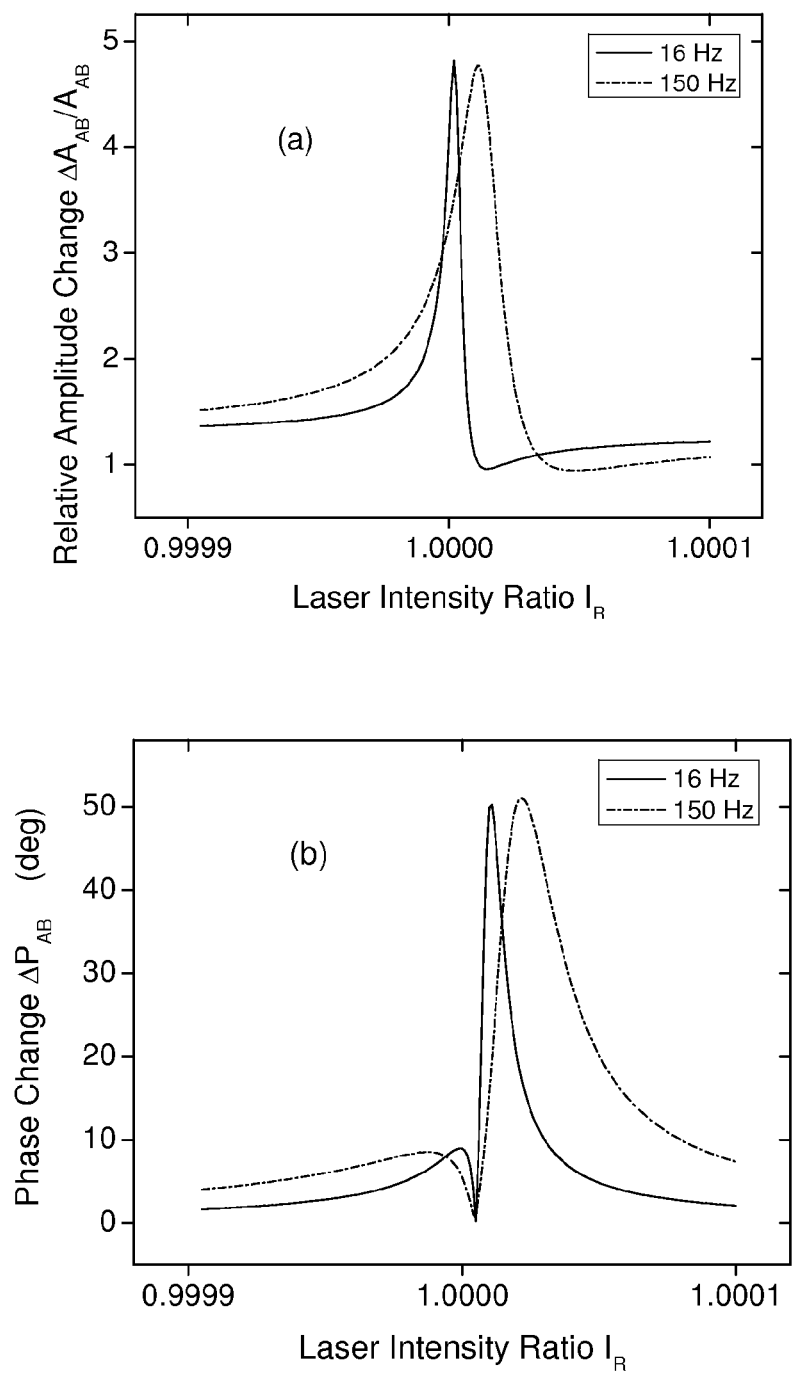
FIG. 5 shows the theoretical dependence of relative amplitude change (a), and phase change (b), on laser intensity ratio IR with modulation frequency as a parameter for 300 mg/dl glucose-water mixture. The modulation frequencies are 16 and 150 Hz.

FIG. 5 shows model predictions, presenting the effects of laser intensity ratio $I_R$ and modulation frequency f on sensitivity to glucose in the 0-300 mg/dl range. It is seen that both amplitude $A_{AB}$ and phase $P_{AB}$ are sensitive to glucose, but the sensitivity and dynamic range are greatly influenced by the relative beam intensity, a fact borne out in experiments presented in the example below. In general, $I_R$ close to 1 is optimal, but equalizing the intensities leads to unacceptably low signal-to-noise ratios. Frequency doesn't affect the peak sensitivity, but it affects the optimal ratio position and high sensitivity (and therefore dynamic) range. Higher frequencies tend to shift the optimal ratio to larger $I_R$ value and broaden the laser intensity ratio range.

While the preceding embodiments involving adjusting the relative intensities of the laser beams provides improved performance, the present inventors have also discovered that improved sensitivity and repeatability can be achieved by controlling the relative amplitude and phase of the individual photothermal signals. Specifically, it has been found that performance improvements can be achieved by maintaining a phase difference of 180° of the individual photothermal signals produced by the first and second modulated beams during calibration. This requirement should be contrasted with the aforementioned requirement that the phase difference between the laser beams should be 180°. By indirectly controlling the relative phase of the two individual photothermal signals, the interference conditions at the sample and the signal-to-noise ratio of the differential photothermal signal can be improved.

Figure 6:
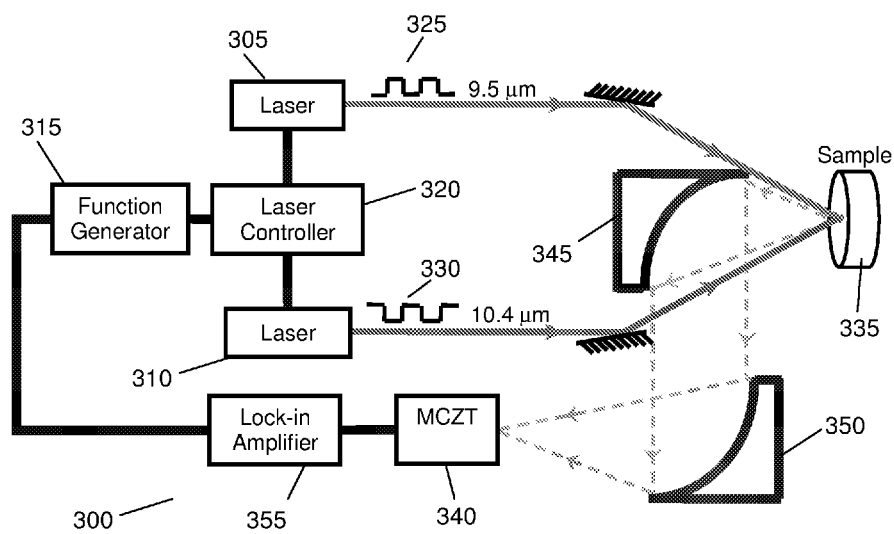
FIG. 6 shows a schematic of the WM-DPTR system in which the relative amplitude and phase of the individual photothermal signals may be controlled to optimize the differential photothermal signal.

An apparatus 300 for performing the present method is shown in FIG. 6. First and second lasers 305 and 310 are provided with an electrical waveform from function generator 315 through laser controller 320. Laser controller 320 controls the intensity and relative phase of modulated beams 325 and 330 emitted by lasers 305 and 315. Lasers 305 and 310 are preferably solid state lasers, and in a preferred embodiment, are quantum cascade lasers.

Modulated beams 325 and 330 are focused onto sample 335, where photothermal radiation is generated. Photothermal power is collected and directed to detector 340 by suitable collection optics, such as parabolic mirrors 345 and 350. Detector 340 is preferable a solid state detector, such as a mercury cadmium zinc telluride detector. The optical bandwidth of the detector is selected to be sensitive to photothermal emission, but to reject scattered light produced by lasers 305 and 310, as noted above. The detected signal is processed by a phase-sensitive system such as lock-in amplifier 355, which is provided with a reference signal by function generator 315, for extracting a phase-sensitive photothermal signal.

First and second lasers 305 and 310 emit light at first and second wavelengths, respectively. As noted above in reference to FIG. 3, the first wavelength (i.e. the wavelength of laser 305) is selected to correspond to a wavelength at which optical radiation will be absorbed by the analyte. Preferably, the first wavelength is selected so that analyte concentrations within a concentration range of interest will cause sufficient absorption of modulated beam 325 to produce detectable thermal-wave emission. The wavelength of the second laser is then selected by requiring that the absorption of the first beam by the analyte exceeds that of the second beam 330 (i.e. the absorption coefficient of the analyte at the first wavelength exceeds that at the second wavelength).

Laser 305 is preferably tuned to a spectral region where the presence of the analyte causes substantial absorption, such as a peak in the absorption spectrum of the analyte. The wavelength of laser 310 (the second wavelength) is preferably tuned to a minimum or off-peak spectral location. A larger difference between the absorption coefficients at the first and second wavelengths will produce a correspondingly larger differential signal. As noted above, the background absorption coefficient (i.e. the absorption coefficient of the reference) need not be equal at the first and second wavelengths. Preferably, the difference between the absorption coefficients of the reference material at the first and second wavelengths is low compared to difference between the absorption coefficients of the analyte alone at the first and second wavelengths, for at least a portion of the analyte concentrations of interest.

More preferably, the absorption coefficients of the reference material at the first and second wavelengths are within an order of magnitude for at least a portion of the analyte concentrations of interest.

It is to be understood that apparatus 300 is only one non-limiting example of the present embodiment, and other devices may be employed to generate the optical beams 325 and 330, provided that the relative intensity and phase can be controlled. Modulated beams 325 and 330 may be obtained from incoherent sources or coherent sources. Preferably, the first and second modulated beams 325 and 330 have lateral intensity profiles that are highly symmetric and free of hotspots. Modulated beams 325 and 330 may be generated by externally chopping continuous-wave beams from a coherent or incoherent source, and the relative phase may be controlled externally. For example, the relative phase may be controlled by an optical delay line, a variable thickness optical element, a variable angle optical element, an electro-optic element, and any other apparatus or device that produces a relative optical path difference between the two beams.

Furthermore, while first and second modulated beams 325 and 330 are described as having first and second wavelengths, respectively, those skilled in the art will appreciate that the first and/or second modulated beams may comprise a range of wavelengths. In such a case, the wavelength as discussed above could be the average wavelength, median wavelength, or any other statistically relevant measure of a characteristic wavelength.

Figure 7:
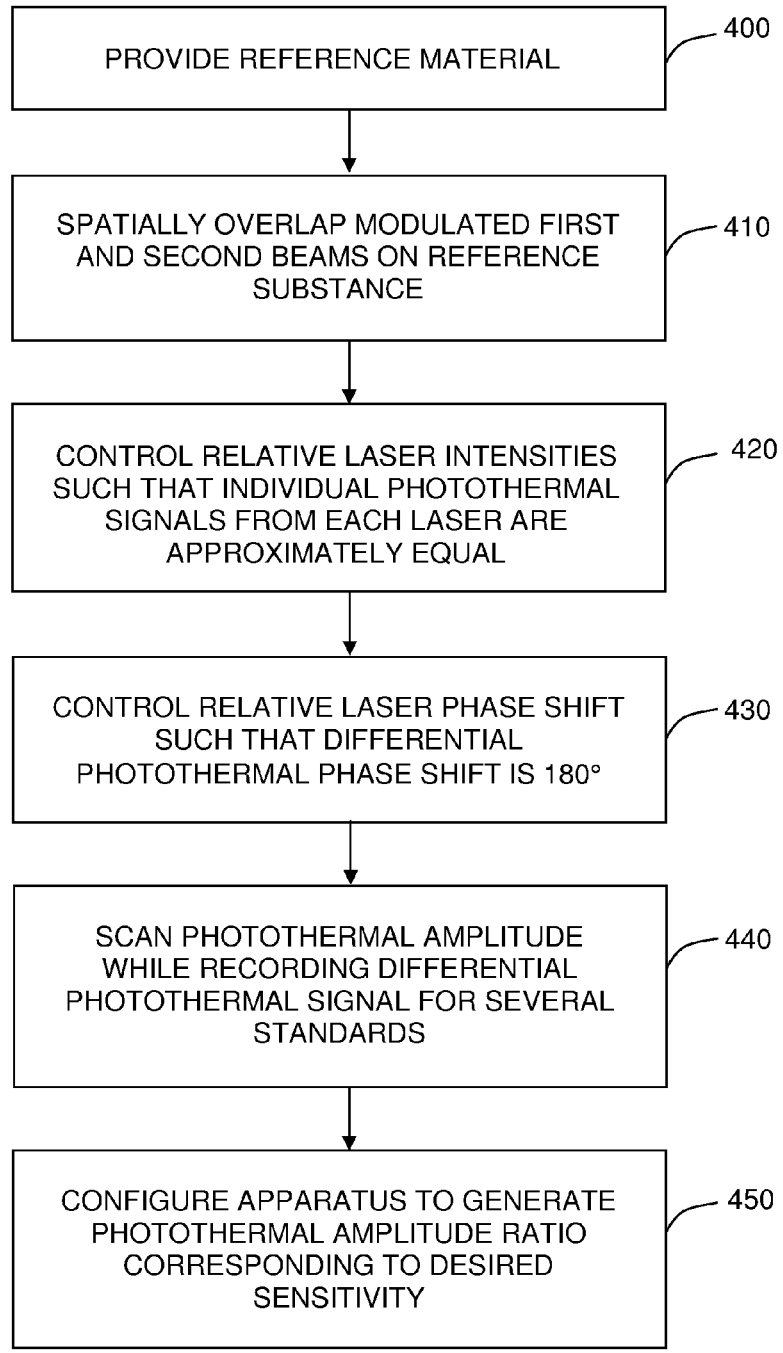
FIG. 7 shows a flow chart describing the modified WM-DPTR method according to an embodiment of the present invention in which the relative amplitude and phase of the individual photothermal signals are controlled to optimize the differential photothermal signal.

Referring to FIG. 7, a flow chart is shown illustrating a calibration method involving the indirect control of the relative amplitude and phase of the photothermal signals. In step 400, a reference material is provided for performing the calibration. The reference material is preferably free of analyte, in which case the absorption spectrum of the reference material is a background absorption spectrum.

In step 410, modulated beams 325 and 330 are directed onto sample 335, and the photothermal responses of both beams are individually measured. In step 420, the intensities of one or both of modulated beams 325 and 330 are controlled to obtain a value of approximately unity for this relative individual photothermal amplitude ratio. Preferably, the intensity of modulated beam 325 is controlled such that the photothermal amplitude for the first modulated beam 325 is near the middle of the full amplitude range for an analyte concentration of interest.

In step 430, the phase difference between the individual photothermal signals generated by modulated beams 325 and 330 is measured, and this phase difference is set to 180° by controlling the relative phase of beams 325 and 330. In the embodiment shown in FIG. 6, the relative phase of beams 325 and 330 may be modified by controlling the relative phases of the electrical waveforms driving lasers 305 and 310. However, it is to be understood that the relative phase of beams 325 and 330 may be manipulated by many other methods, such as using a variable optical delay or an electro-optic device.

With the relative individual photothermal phase set to 180° and the relative amplitudes of the individual photothermal signals approximately equal, the system is calibrated. To obtain a more accurate calibration for providing high sensitivity, the relative amplitudes of the individual photothermal signals are modified based on measurements of standards having known analyte concentrations. This step improves the performance of the system because the optimal individual photothermal signal amplitude ratio may be dependent on the analyte concentration, with different concentration ranges having different optimal amplitude ratios. Preferably, prior to measuring standards, the relative individual photothermal amplitude ratio is scanned (by controlling the intensities of modulated beams 325 and 330) over a small range close to unity, for example, 0.95 to 1.05, and it is verified that the phase difference between the individual photothermal signals is 180° over this range.

In step 440, standards containing known concentrations of analyte are measured, and the relative individual photothermal amplitude ratio is scanned near unity (again, by controlling the intensities of modulated beams 325 and 330) for each standard while measuring the differential photothermal signal. The calibration measurements may then be employed to when measuring unknown samples to select a suitable relative individual photothermal amplitude ratio (or equivalently, each modulated beam intensity ratio) for a given concentration range of interest, as shown in step 450. For example, over a given analyte concentration range, an optimal relative photothermal amplitude ratio may be 0.97, while value of 1.02 may be more appropriate for a different concentration range. Preferably, the calibration measurements are employed to generate a series of calibration curves, with a different calibration curve for each relative individual photothermal amplitude ratio (or equivalently, each modulated beam intensity ratio).

Numerical simulations were performed to investigate the impact of the individual photothermal phase difference on the measured differential photothermal signal. The exemplary system chosen for the simulations involved glucose as the analyte and water as the reference material.

Figure 8:
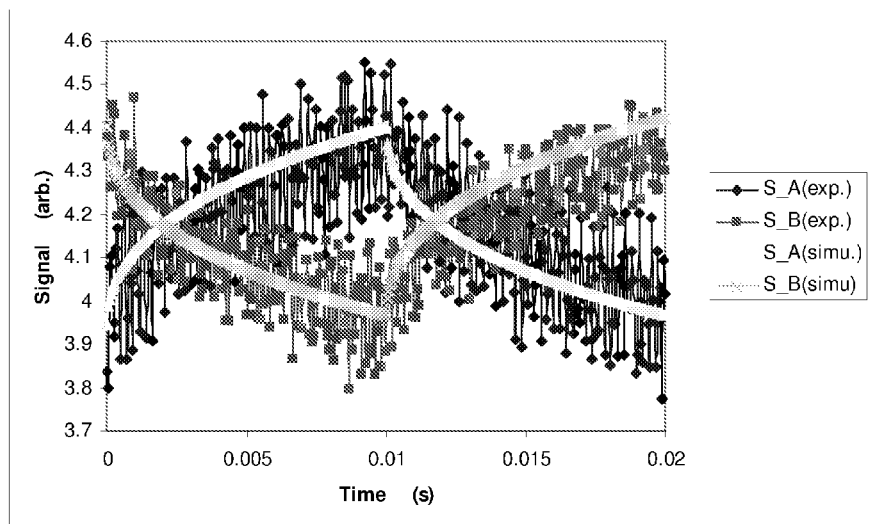
FIG. 8 plots the photothermal waveforms generated from water. S_A and S_B are signals from the first and second lasers, respectively.

FIG. 8 shows the individual photothermal responses in the time domain (in arbitrary units), plotted along with experimental data using the system of FIG. 6, for water in the absence of glucose. The signals A and B are the time domain signals individually produced by lasers A and B, which are controlled to generate a 180° relative phase shift as shown.

Figure 9:
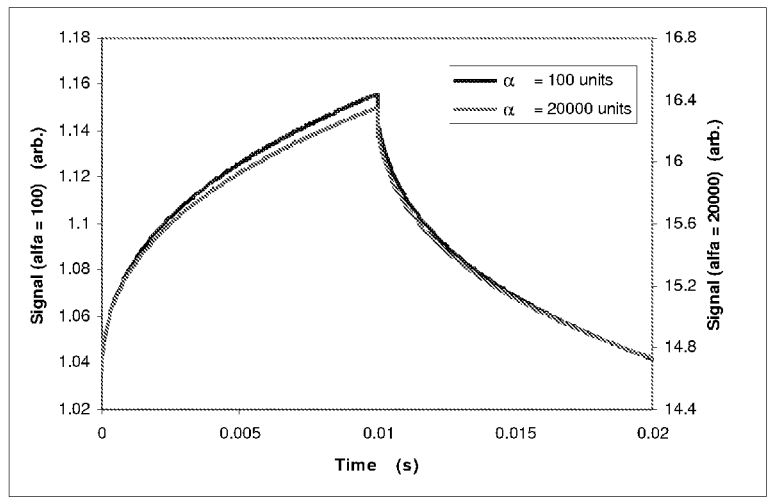
FIG. 9 plots the thermal-property-change effect on photothermal waveforms according to a numerical simulation. $\alpha$ is thermal diffusivity of the sample (glucose will cause this parameter to change).
Figure 10:
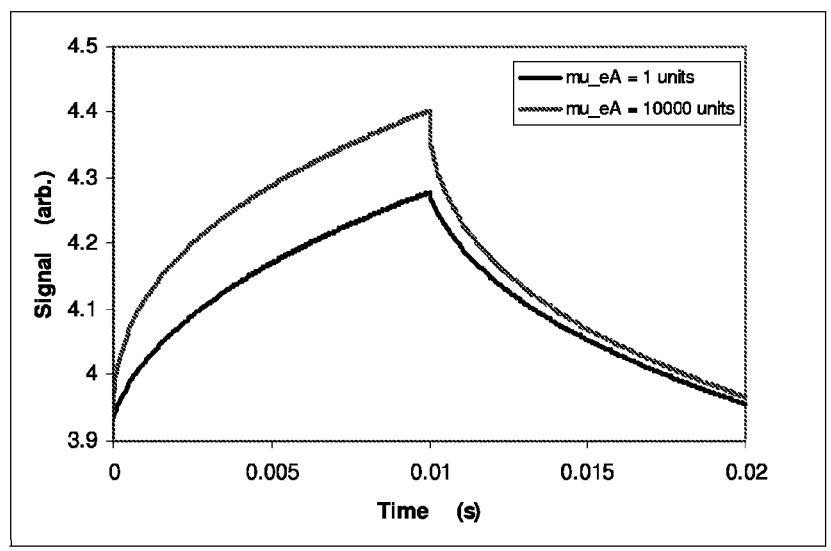
FIG. 10 plots the optical-property-change effect on photothermal waveforms according to a numerical simulation. mu_eA is optical absorption coefficient of the sample at the first laser wavelength (glucose will cause this parameter to change).

The effect of the thermal diffusivity on the simulated waveform is shown in FIG. 9, where the time domain photothermal signal from one laser is plotted for two different values of the thermal diffusivity. Similarly, FIG. 10 illustrates the effect of a change in the optical absorption coefficient on the time domain photothermal signal generated by an individual laser source. These two figures highlight the effect of the optical and thermal properties on the amplitude and phase of the photothermal signal.

Figure 11:
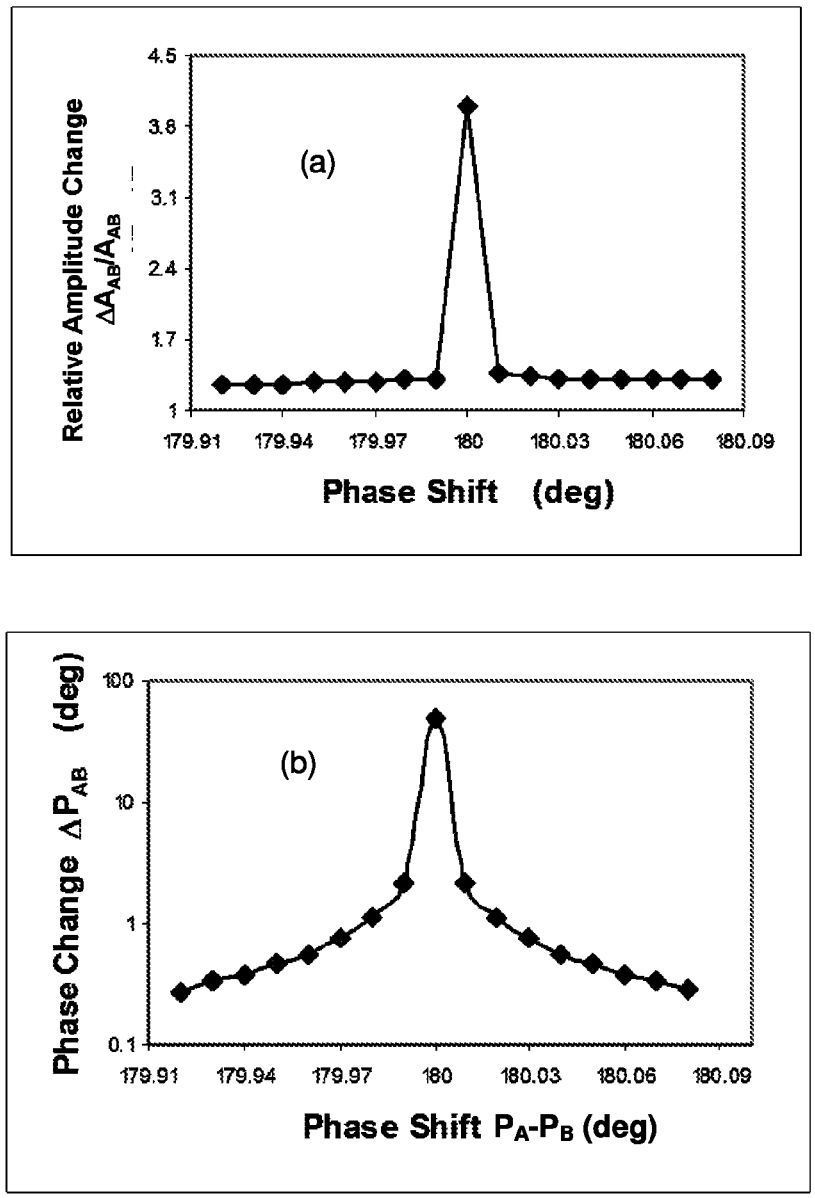
FIG. 11 shows the relative amplitude change $\Delta A_A/A_B$ (a) and phase change $\Delta P_{AB}$ (b) as a function of reference phase shift $P_A-P_B$ from pure water (0 mg/dl) to 300 mg/dl glucose concentration according to a numerical simulation. The maximum glucose sensitivity peaks at phase shift=180°. Phase shift has stronger effect on phase maximum glucose sensitivity than on amplitude maximum glucose sensitivity. The maximum glucose sensitivity is defined as the maximum signal change from pure water to 300 mg/dl glucose concentration change across the amplitude ratios.

FIG. 11(a) plots the effect of the phase shift between the individual photothermal signals on the relative amplitude change for a glucose concentration of 300 mg/dl. In FIG. 11(b), it is clearly seen that the effect of the phase shift between the individual photothermal signals on the differential photothermal phase shift can be many orders of magnitude higher than the effect of the phase shift on the amplitude. These results strongly support the inclusion of the step of generating a 180° phase shift for optimal sensitivity.

Figure 12:
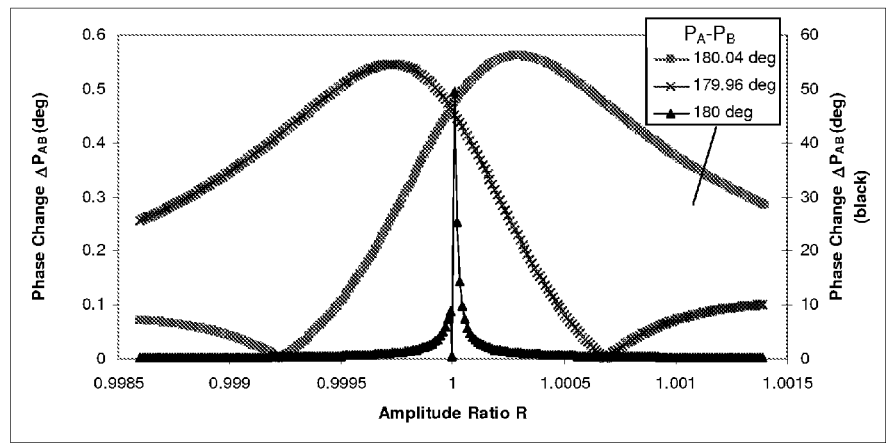
FIG. 12 illustrates that the water baseline phase shift $P_A-P_B$ not only affects the maximum sensitivity to glucose, but also the position of the maximum glucose sensitivity along the amplitude ratio axis (simulation). The maximum glucose sensitivity position will shift to R>1 if the phase shift is larger than 180°, otherwise it will shift to R<1. The simulation was done with 300 mg/dl glucose concentration.

In FIG. 12, the photothermal phase change $\Delta P_{AB}$ obtained for different values of phase shift $P_A$-$P_B$ between the individual photothermal signals is plotted as a function of the individual photothermal signal amplitude ratio R. It can be seen that the value of phase shift between the individual photothermal signals can have a strong effect on the position of the maximum glucose sensitivity in terms of the individual photothermal signal amplitude ratio.

Figure 13:
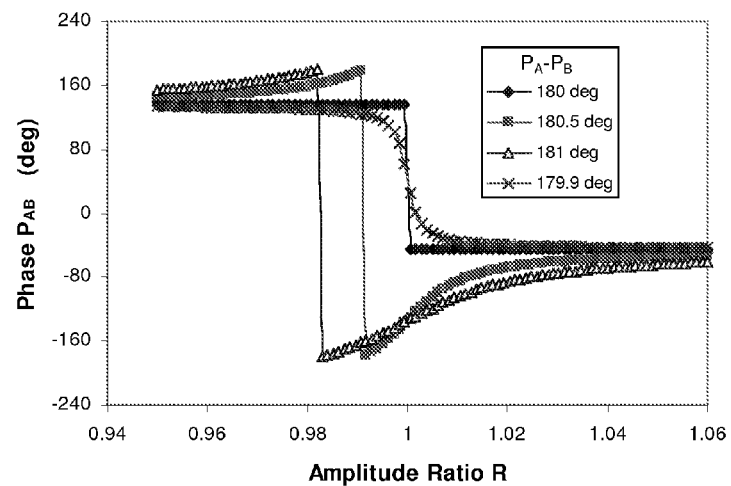
FIG. 13 illustrates the phenomenon of phase transition (flip-over), which enables another potential glucose concentration measurement method. Differential phase $P_{AB}$ for various phase shifts $P_A-P_B$ exhibits a 360° flip-over at different amplitude ratios. Different (high) glucose concentrations may cause phase flip-over at different amplitude ratios.
Figure 14:
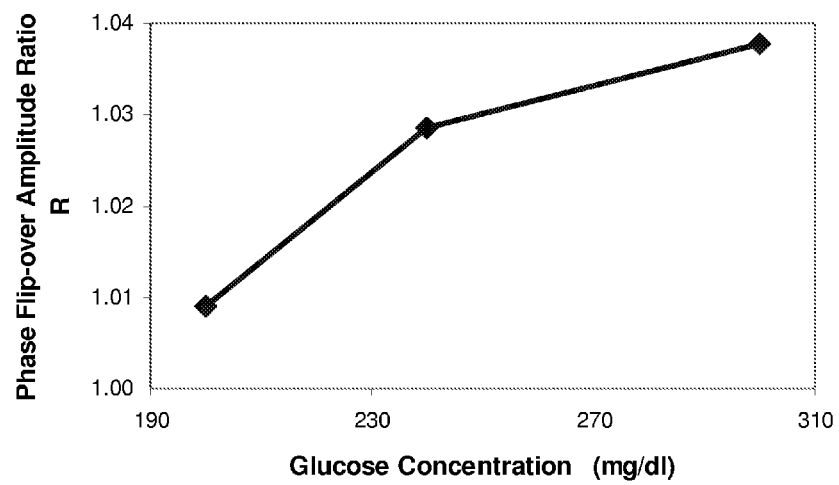
FIG. 14 plots experimental results for phase transition (flip-over) glucose detection. Phase flip-over is sensitive to high glucose concentrations.

FIG. 13 provides simulation results that demonstrate the effect of the phase shift between the individual photothermal signals on the amplitude ratio at which a phase flip-over occurs. These results suggest that amplitude ratio at which the phase flip-over occurs, and its dependence on glucose concentration, can be used to measure the glucose concentration. FIG. 14 provides experimental results of such an embodiment, where the phase flip-over amplitude ratio is plotted as a function of glucose concentration. The experimental results indicate that a sensitive and one-to-one dependence is obtained.

Figure 15:
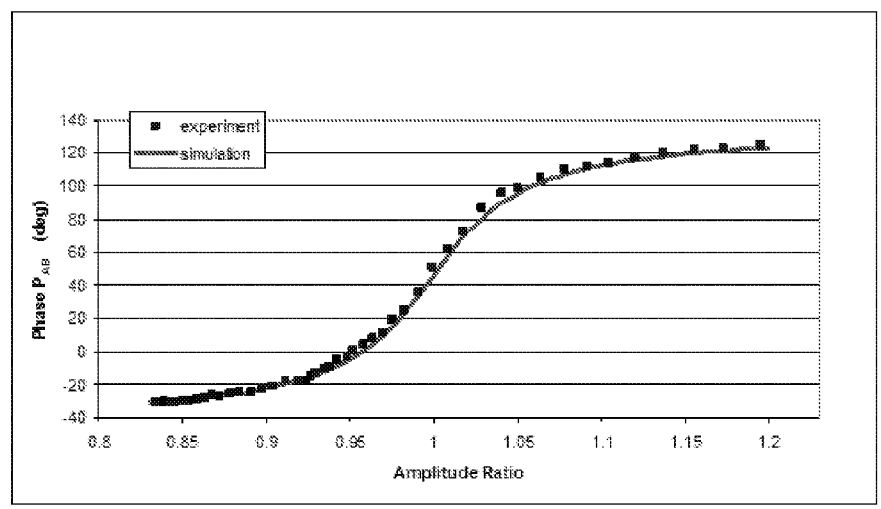
FIG. 15 plots experimental data taken with laser phase shift at 180°, which were fitted well with the simulation model with photothermal signal phase shift set at 182.43°, validating the concept that optical and photothermal phase shifts are not the same.

The importance of controlling the relative phase between the modulated beams to obtain a 180° relative phase lag is highlighted in the simulation plotted in FIG. 15. The Figure plots the photothermal phase as a function of the amplitude ratio, showing both experimental data and a simulated fit. Although the phase delay between the optical modulated beams was 180°, the actual relative phase difference between the two individual photothermal signals was inferred from the simulated results to be 182.43°. This result clearly shows that merely specifying a 180° laser phase shift is insufficient to realize an actual 180° of the individual photothermal signals.

The lack of agreement between the optical beam phase difference and the phase difference of the individual photothermal signals can arise from several potential sources. Without being limited to theory, it is believed that the additional difference may be due to an additional phase delay that can arise during the propagation of the thermal waves. The additional phase difference can also arise from the two optical sources (e.g. lasers) being operated at different conditions. For example, if the two sources are semiconductor lasers, applying different voltages to the two lasers can cause an additional phase delay relative to the phase delay provided by the function generator.

Figure 16:
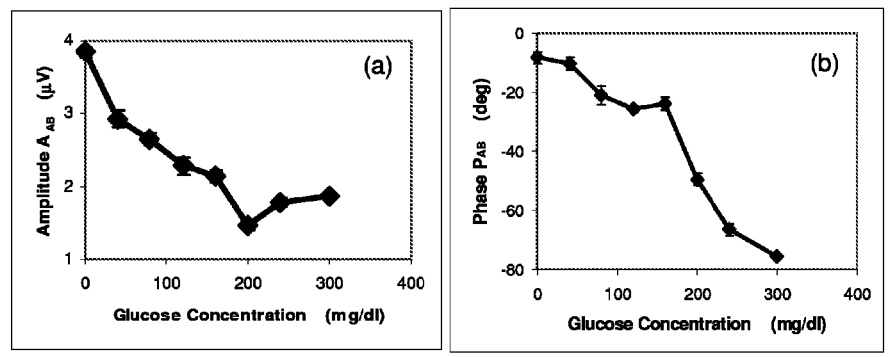
FIG. 16 plots experimental data taken using the apparatus shown in FIG. 6, illustrating glucose detection at R=0.999 and phase shift $P_A-P_B$=180°. Amplitude and phase trends are complementary in glucose measurements. Amplitude is more sensitive at low glucose concentrations while phase is more sensitive at high glucose concentrations. One-to-one correspondence between signal and glucose concentration throughout the entire concentration range (0-300 mg/dl) can be attained by simultaneous use of both amplitude and phase curves.
Figure 17:
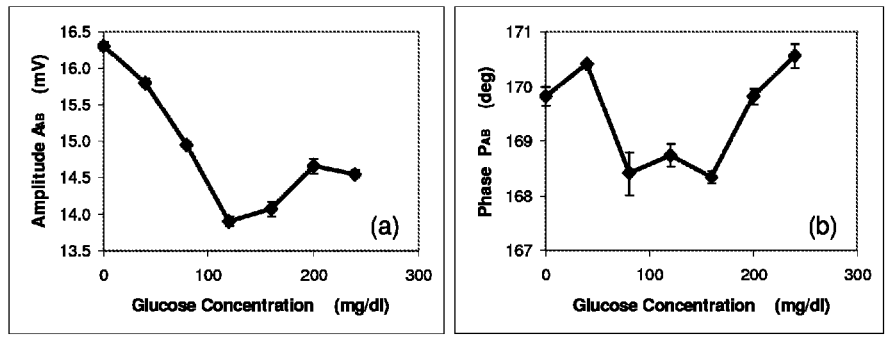
FIG. 17 plots experimental data taken using the apparatus shown in FIG. 6, demonstrating glucose detection at R=1.039 and phase shift $P_A$-$P_B$=180°. Amplitude is very sensitive at low glucose concentrations (hypoglycemic to normal) but phase is saturated. Phase is sensitive at higher glucose concentrations.
Figure 18:
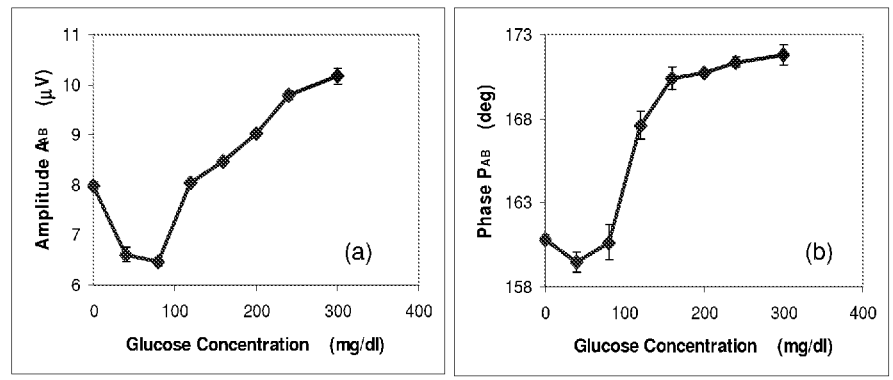
FIG. 18 plots experimental data taken using the apparatus shown in FIG. 6, demonstrating glucose detection at R=1.014 and phase shift $P_A$-$P_B$=180°. Amplitude is very sensitive at high glucose concentrations while phase is more sensitive at medium glucose concentrations. Both signal channels are monotonic with glucose concentration in the range>80 mg/dl (normal to hyperglycemic).

The experimentally measured dependence of the differential photothermal amplitude and phase on glucose concentration is plotted in FIGS. 16-18 for a number of different amplitude ratios. The measured results were obtained using the apparatus shown in FIG. 6, and the phase difference between the individual photothermal signals was set at 180° for all measurements, as per the method illustrated in FIG. 7. The results clearly show that the sensitivity of the measured amplitude and phase over various glucose concentration ranges can be modified by selecting different values of the amplitude ratio.

While the above embodiments pertained to a reference that is substantially free of analyte, it is to be understood that the reference may comprise a known analyte concentration. The known analyte concentration may be, for example, a baseline concentration relevant to a particular material system under analysis.

In preferred embodiments, the analyte is glucose and the reference substance is tissue, water, blood (serum, whole blood or synthetic blood), or a substance mimicking the absorption spectrum of tissue or a biological fluid. However, the embodiments disclosed herein may be applied to the measurement of a wide range of analytes in a wide range of substances. The substance need not be a tissue, and may be any substance capable of generating thermal waves, such as a solid or a liquid. Exemplary non-limiting applications include the measurement of chemical and biochemical analytes within biological or other substances, water quality monitoring, industrial process control monitoring of the concentration of chemical species (i.e. analytes) within substances (either to monitor the presence of desired species or to detect contaminants), and the detection of chemical warfare agents or species that may represent biothreats, such as sarin or anthrax spores.

The aforementioned methods may be applied to material systems where specific absorption bands can be monitored against a constant background absorption spectrum, or a changing background absorption spectrum where the rate of change of the absorption coefficient is slow compared to the structure of the analyte absorption band (or bands), including cases with overlapping background absorption features of absorption coefficients higher or much higher than the analyte or material system, which, however, remain fixed with changes in the absorption coefficient of the analyte, for example, due to concentration changes.

The following examples are presented to enable those skilled in the art to understand and to practice the present invention. They should not be considered as a limitation on the scope of the invention, but merely as being illustrative and representative thereof.

EXAMPLE

Figure 19:
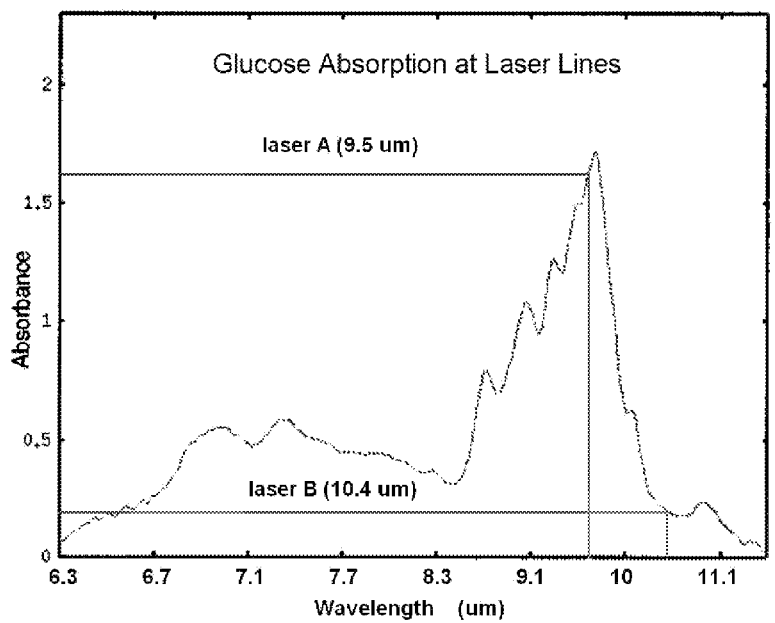
FIG. 19 shows the glucose absorption spectrum in the mid-IR. Two laser lines, $\lambda_A$=9.5 μm and $\lambda_B$=10.4 μm, coincide with the peak and the base of the dominant glucose absorption band.

WM-DPTR Method for the Non-Invasive Detection of Glucose Using Intensity Control The modified WM-DPTR method, when adapted specifically for the measurement of glucose, consists of the out-of-phase modulated excitation at two discrete wavelengths, preferably 9.5 µm and 10.4 µm and/or 8.5 µm (preferably near the peak and the baseline of the aforementioned glucose absorption band, respectively, FIG. 19). Two laser beams (~45 mW each) at 9.5 µm and 10.4 µm were generated by two quantum cascade lasers (QCL) or alternatively, $CO_2$ lasers as disclosed in US20070213607, resulting in a differential blackbody (Planck) emission and a thermal-wave up-conversion process detected via a broadband, thermally-sensitive detector such as a HgCdZnTe (MCZT) detector (preferably with a 2-6 µm spectral detection bandwidth).

The differential method suppresses the strong background signal due to water absorption while the detector spectral bandwidth, which rejects the incident beams, eliminates source-detector interference, thus greatly enhancing glucose detection sensitivity.

The measurement results discussed below from aqueous glucose mixtures (0-440 mg/dl) demonstrate that both amplitude and phase of the WM-DPTR signal can be used for glucose detection. The dynamic range and the sensitivity of glucose detection can be controlled by judicious selection of laser intensity ratio and modulation frequency. The results also demonstrate the distinct advantages of the modified WM-DPTR method over single-ended (i.e. single laser beam) photothermal methods and purely optical or thermal methods.

Figure 20:
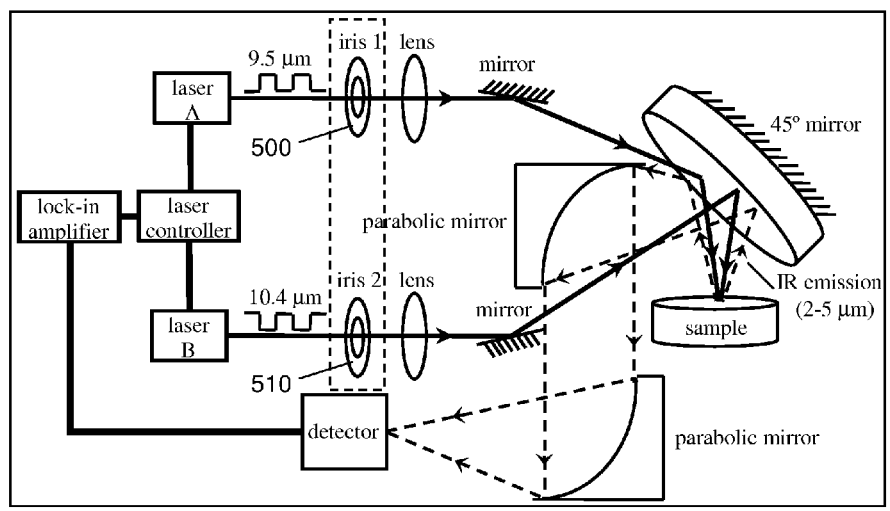
FIG. 20 shows a schematic diagram of the inventive WM-DPTR system as applied to the measurement of glucose according to an embodiment of the present invention.

FIG. 20 is the experimental set-up of the modified WM-DPTR system. Two out-of-phase modulated mid-IR laser beams (QCL "laser A" (9.5 µm) and "laser B" (10.4 µm), both commercially available), are focused onto a sample with a pair of lenses, producing overlapping spots on the sample. The generated IR (Planck) emission is collected by a 45° mirror and focused onto a MCZT detector (PVI-2TE-5, Vigo Systems, Poland) through a pair of off-axis paraboloidal mirrors.

The signal from the detector is then sent to a lock-in amplifier for demodulation. To achieve the intensity and spatial control required by the modified WM-DPTR method, the laser intensity ratio on the sample is strictly controlled with a pair of irises 500 and 510 positioned in front of the lasers. It was found that controlling the diameter of one iris relative to another iris was critical to the performance of the instrument, and iris 2 was motorized with diameter resolution 1.7 µm.

The laser beam with $\lambda_A$=9.5 µm near the peak and the out-of-phase beam with $\lambda_B$=10.4 µm at the baseline of the mid-IR glucose absorption band, generate two out-of-phase photothermal signals $S_A$ and $S_B$ dependent on the optical and thermal properties of the sample. $S_A$ and $S_B$ denote the full complex signal expression, e.g. $S_A = A_A e^{iP_A}$. The optical absorption coefficient, $\mu_a$, and thermal effusivity, and $\mu_{aA}$ are glucose-concentration and background absorption dependent, while, $\mu_{aB}$ is only background-dependent but glucose-concentration independent. $\mu_{aA}$ and $\mu_{aB}$ represent absorption coefficients of a glucose-background (water, in our case) mixture at the two laser wavelengths $\lambda_A$ and $\lambda_B$, respectively. Thus the resulting differential signal $S_{AB} = S_A - S_B$ minimizes the background water absorption/emission effects, suppresses the overall signal range (from mV to µV) and is related to the glucose concentration of the sample with much higher sensitivity than either signal $S_A$ or $S_B$. $S_{AB}$ can be expressed by two parameters: amplitude $A_{AB}$ and phase $P_{AB}$.

The water-glucose mixtures were obtained by dissolving D-glucose (Sigma, USA) in deionized water. Accurate glucose concentrations of the mixtures (0-440 mg/dl) were determined using a biochemistry analyzer (YSI 2700S, Life Sciences, USA). The glucose detection range 0-20 mmol/l (0-360 mg/dl) was chosen to monitor both hyperglycemia and hypoglycemia, the two problematic ranges in diabetes blood glucose regulation.

Figure 21:
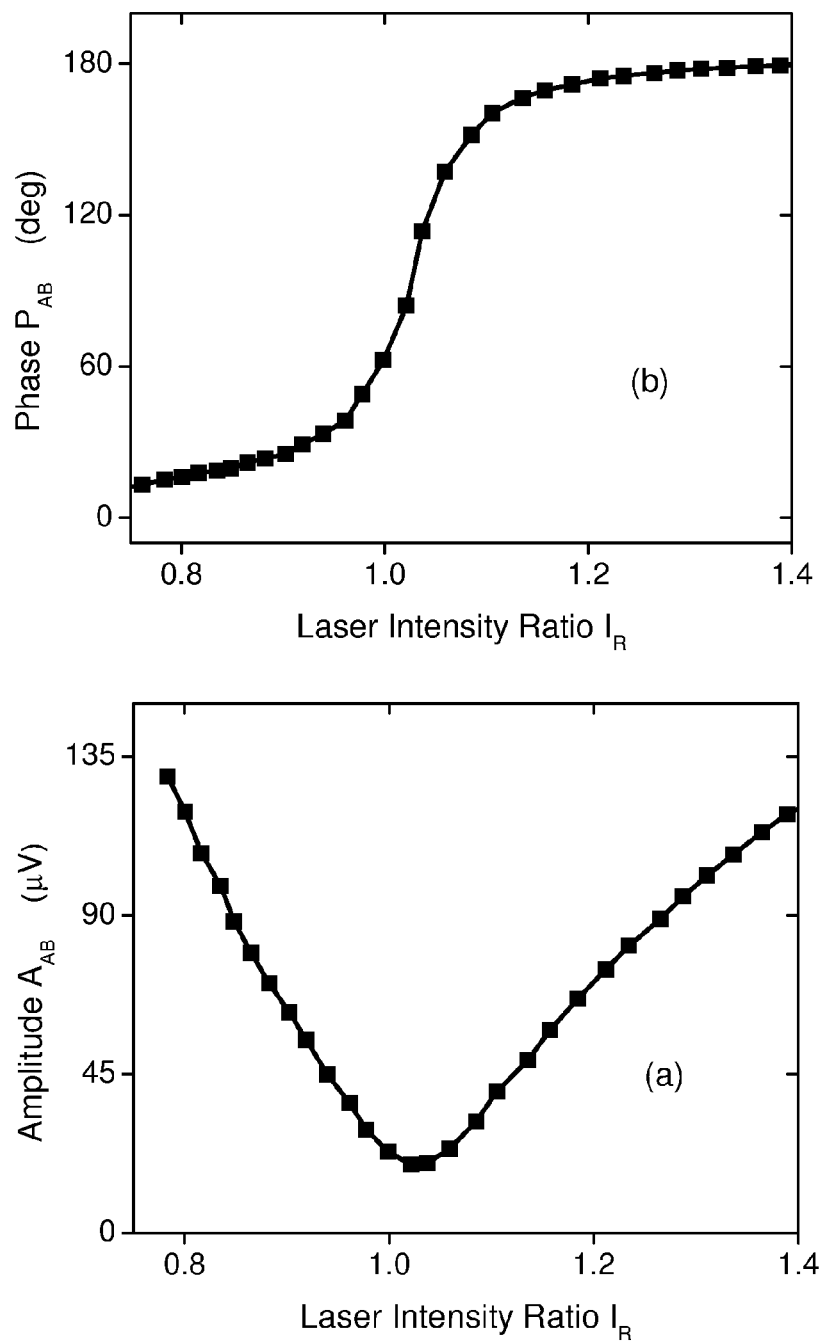
FIG. 21 shows the influence of laser intensity ratio $I_R$=$I_A$/$I_B$ on pure water solution (glucose concentration=0 mg/dl) WM-DPTR signals at modulation frequency f=16 Hz; (a) amplitude vs. laser intensity ratio, (b) phase vs. laser intensity ratio.

FIG. 21 shows how the laser intensity ratio $I_R = I_A/I_B$ affects the measured differential signal $A_{AB}$ and $P_{AB}$ of the strongly absorbing water baseline (glucose concentration=0 mg/dl). It shows that $A_{AB}$ is non-monotonic with laser intensity ratio, $I_R$~1 being the transitional point. $P_{AB}$ approaches saturation when $I_R$>>1 or $I_R$<<1. There is a ~180° transition at $I_R$~1. The amplitude minimum is not zero and does not occur at $I_R$=1 precisely, because there is a water absorption coefficient difference between $\lambda$=9.5 µm and 10.4 µm excitation. Nevertheless, for sensitive and monotonic differential glucose measurements (small interference of the water baseline), $I_R$ should be selected close to unity, so as to make $A_{AB}$ monotonic and take advantage of the very large phase change. In practice, $I_R$=1 is not the optimal baseline position because the low differential signal $S_{AB}$ results in very poor signal-to-noise ratio in both amplitude and phase channels.

Figure 22:
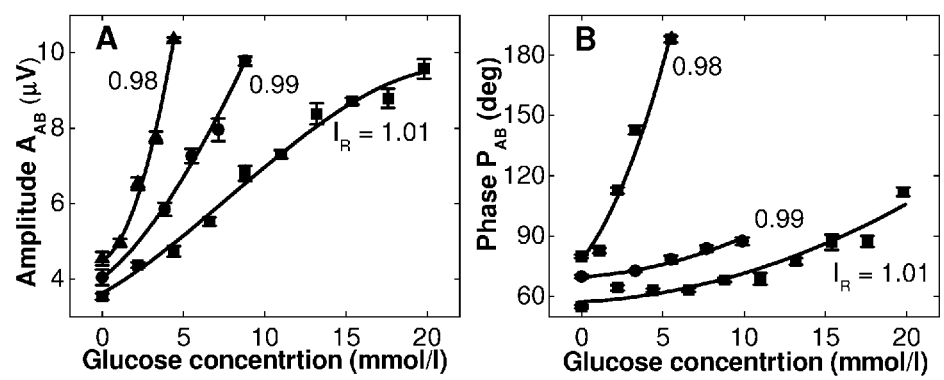
FIG. 22 shows the effect of laser intensity ratio on glucose measurement sensitivity and detection range at modulation frequency f=49 Hz for $I_R$=0.98, 0.99 and 1.01; (a) amplitude vs. glucose concentration. (b) phase vs. glucose concentration. Each datum is an average of five measurements. Changes in $I_R$ were made through fine adjustment of iris 2, FIG. 20.

FIG. 22 is the measured WM-DPTR amplitude and phase vs. glucose concentration at intensity ratios $I_R$=1.01, 0.99 and 0.98 and modulation frequency 49 Hz. It is seen that both amplitude and phase of the differential signal are sensitive to glucose. Since the amplitude of the differential signal will not be affected by the skin color of patients due to negligible melanin absorption in the wavelength range above 1.1 µm (18,19), both amplitude and phase can be used for optimally reliable glucose concentration diagnosis in a clinical setting. It is further observed that with decreasing intensity ratio, the sensitivity increases greatly at the expense of signal dynamic range. The highly sensitive measurement capability in low glucose concentration range is very attractive due to the lack of non-invasive methods for hypoglycemia monitoring below 3.85 mmol/l (70 mg/dl) for adults and around 1.65-2.2 mmol/l (30-40 mg/dl) for newborn infants (20).

Figure 23:
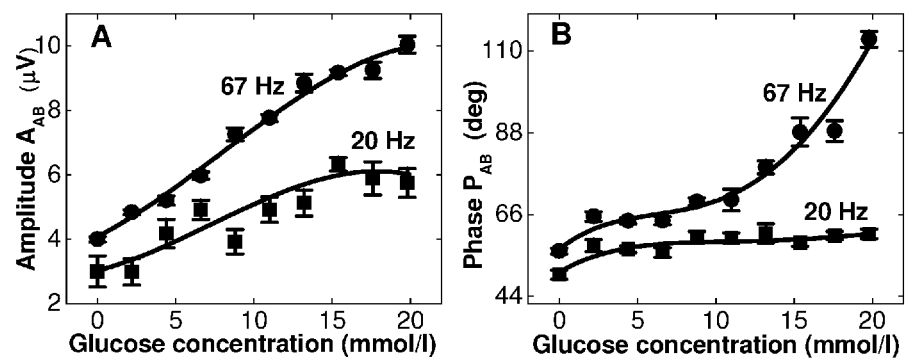
FIG. 23 shows the effect of modulation frequency on glucose measurement sensitivity at intensity ratio $I_R$=1.01, f=20 Hz and 67 Hz; (a) amplitude vs. glucose concentration, (b) phase vs. glucose concentration. Each datum is an average of five measurements

Shown in FIG. 23 are measurements at fixed laser intensity ratio $I_R$=1.01 and two modulation frequencies, 67 Hz and 20 Hz. Both amplitude and phase are more sensitive at higher frequency. This is in agreement with simulation results (FIG. 5) showing that the detection sensitivity at different modulation frequencies does not peak at the same intensity ratio. FIG. 23 shows very complementary sensitivity to glucose between amplitude and phase across the full range of concentration.

Figure 24:
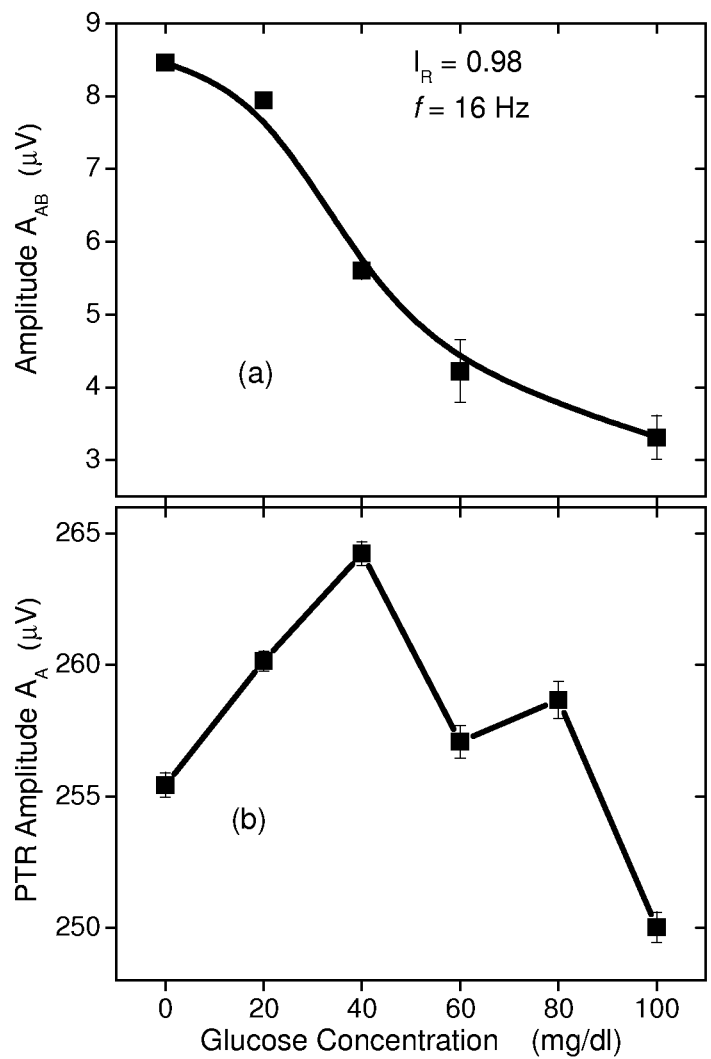
FIG. 24 shows a comparison between the amplitude of the (a) differential WM-DPTR method and the (b) single-ended photothermal radiometric (PTR) method for low concentration glucose detection (0-5.5 mmol/l (0-100 mg/dl)) at modulation frequency f=16 Hz.
Figure 25:
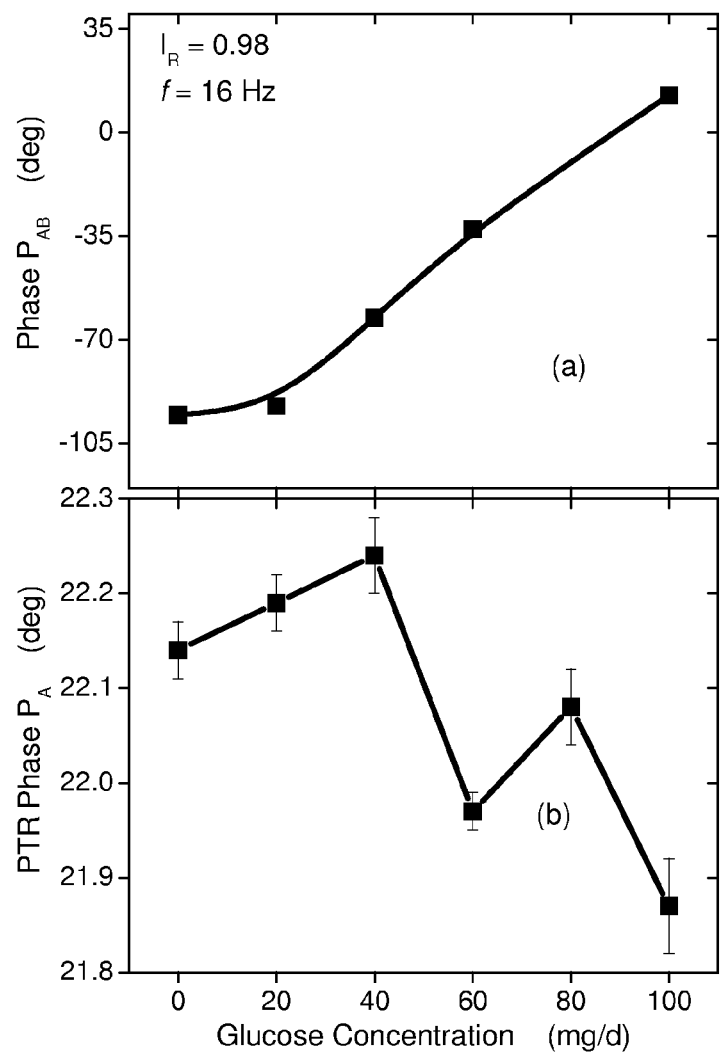
FIG. 25 shows a comparison between the phase of the (a) differential WM-DPTR method and the (b) single-ended PTR method for low concentration glucose detection (0-5.5 mmol/l (0-100 mg/dl)) at modulation frequency f=16 Hz.

The significance of the WM-DPTR method in non-invasive glucose detection can be seen from comparison measurements with the conventional single-ended photothermal radiometric (PTR) method and purely thermal-wave PTR. FIGS. 24 and 25 are the comparison of differential amplitude and phase signals ($A_{AB}$, $P_{AB}$) at intensity ratio $I_R$=0.98 with PTR single-ended signals ($A_A$, $P_A$) (with only peak absorption laser A incident on the sample) in the low-concentration 0-100 mg/dl glucose range. The figures show that the differential method is much more sensitive than the single-beam PTR method: 100 mg/dl glucose solution induces ~61% monotonic decrease in the differential amplitude $A_{AB}$, but only ~2% non-monotonic variation in the PTR amplitude, $A_A$. The same amount of glucose solution induces ~108 degrees monotonic change in the differential phase $P_{AB}$, but <1 degree non-monotonic variation in the PTR phase $P_A$.

Figure 26:
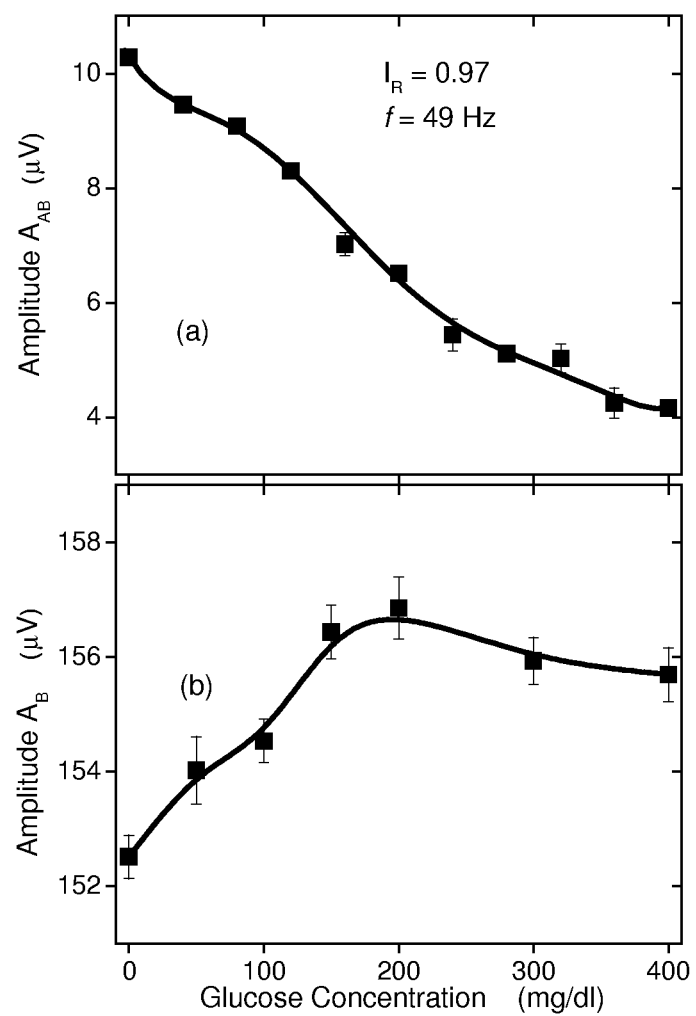
FIG. 26 shows a comparison between the amplitude of the (a) differential WM-DPTR method and the (b) single-ended PTR method for glucose detection across the clinical human reference range of concentrations (0-22.0 mmol/l (0-400 mg/dl)) at modulation frequency f=49 Hz.
Figure 27:
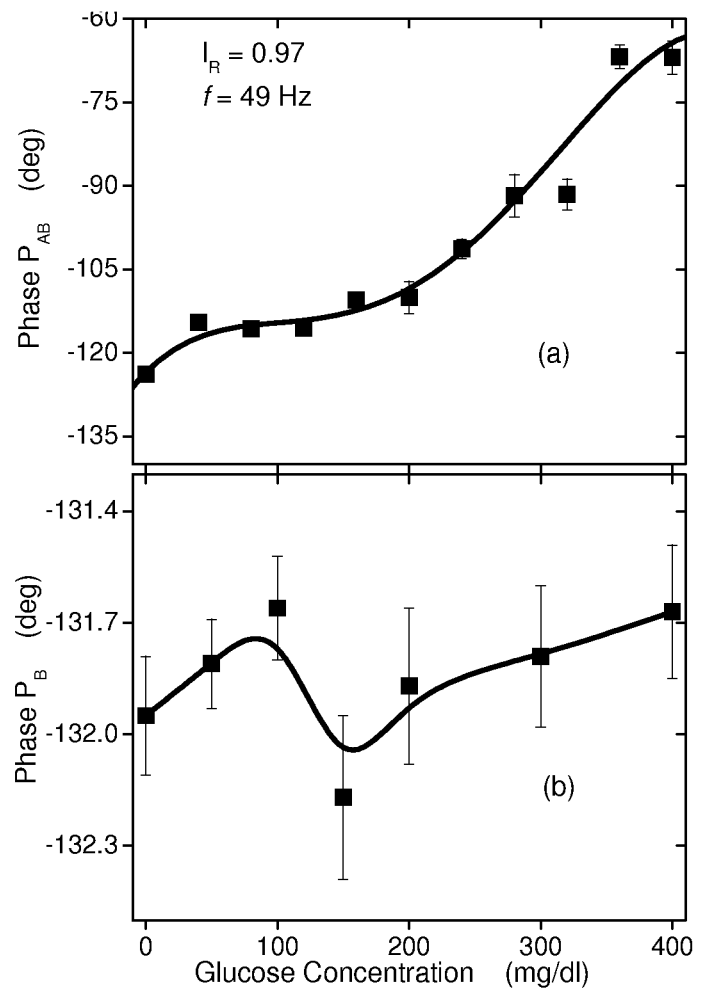
FIG. 27 shows a comparison between the phase of the (a) differential WM-DPTR method and the (b) single-ended PTR method for glucose detection across the clinical human reference range of concentrations (0-22.0 mmol/l (0-400 mg/dl)) at modulation frequency f=49 Hz.

FIGS. 26 and 27 are the comparison between WM-DPTR differential signals ($A_{AB}$, $P_{AB}$) at the intensity ratio $I_R$=0.97 and single-ended purely thermal-wave signals ($A_B$, $P_B$). The latter signals were obtained with only laser B incident on a thermally very thin anodized aluminum foil in contact with the surface of the glucose solution in the 0-400 mg/dl glucose concentration range, so as to eliminate optical absorption effects from the signal. Once again, the differential method exhibits much higher sensitivity than the single laser thermal-wave method: 400 mg/dl glucose solution induces ~60% monotonic change in differential amplitude $A_{AB}$, but only ~2% non-monotonic variation in single laser amplitude $A_B$. The same amount of glucose solution induces ~57 degree monotonic change in differential phase $P_{AB}$, but <1 degree non-monotonic variation in single laser thermal-wave phase $P_B$. These large quantitative differences between prior art methods and the modified WM-DPTR method according to embodiments of the present invention are further shown below in Table 1 (also, see the Discussion section below).

TABLE 1

Resolution comparison in glucose detection

| Glucose Concentration (mmol/l (mg/dl)) | Resolution (mmol/l (mg/dl)) | | | | |
|---|---|---|---|---|---|
| | WM-DPTR | | LPAS(9) | Absorption(10) | Polarimetry(20) |
| | A | P | | | |
| 0-5.5 (0-100) | 0.22 (3.9) | 0.07 (1.3) | 0.92 (18.4) | 1.38 (25) | 3.08 (56) |
| 3.85-8.8 (70-160) | 0.25 (4.5) | 0.55 (10.1) | | | |
| 4.4-15.4 (80-280) | 0.43 (7.8) | 0.87 (15.7) | | | |
| 4.4-19.8 (80-360) | 0.57 (10.4) | 0.64 (11.6) | | | |

The glucose sensing capability of the WM-DPTR method is rooted in the combined optical and thermal property (absorption coefficient $\mu_a$ and thermal effusivity e) changes of the liquid sample with glucose concentration, which are also the bases for conventional optical and thermal-wave methods. However, the direct purely optical methods (such as transmission measurements) and purely thermal-wave methods (thermal effusivity measurements) are much less sensitive than WM-DPTR. As shown in FIG. 4, a 360 mg/dl change in glucose concentration results in ~83% change in thermal effusivity and ~2.8% change in optical absorption coefficient, both contributing to ~170% change in WM-DPTR amplitude (FIG. 24).

Among the current non-invasive glucose detection technologies in the MIR range ~9.5-9.6 μm, laser photoacoustic spectroscopy (8,9) and thermal gradient spectroscopy (12) are the two most sensitive back-propagation techniques reported to-date which can be viable for clinical applications. WM-DPTR outperforms them both with superior signal accuracy, sensitivity and resolution. The non-contacting back-propagation detection character makes WM-DPTR very viable for single-sided clinical applications, whereas photoacoustic and thermal gradient methods (both contacting techniques) suffer from large water baseline variations due to moisture accumulation at the contacting interface. Moisture accumulation can generate large false positive or negative baseline contributions to the glucose-dependent signals and seriously compromise the calibration precision of instruments built on those principles leading to inaccurate predictions. For sensitivity and resolution, we compared the performance in glucose detection of three highly sensitive non-invasive techniques: photoacoustics (9), optical absorption/transmission (10), and polarimetry (21). We worked with the published signal vs. glucose concentration plots and their published uncertainty (error bars). All the samples in the measurements were aqueous glucose phantoms except for the photoacoustic method which used blood serum. Table 1 shows the resolution comparison between WM-DPTR and the above three techniques in the 0-20 mmol/l (0-360 mg/dl) glucose range. WM-DPTR exhibits distinct advantages over a wider glucose concentration range with best resolution (between amplitude and phase) ranging from 0.25 mmol/l (4.6 mg/dl) in the hyperglycemic and normal range, up to 0.07 mmol/l (1.3 mg/dl) in the hypoglycemic range. The other three techniques exhibit best resolution below 0.92 mmol/l (18.4 mg/dl) and only in the normal—hyperglycemic range.

The modified WM-DPTR method is a very sensitive method for glucose detection in aqueous phantoms in the clinically relevant range and this example has demonstrated its superior sensitivity and resolution when compared with current non-invasive and clinically feasible techniques. The amplitude and phase of the WM-DPTR signal act as two complementary glucose metrics and yield reliable results.

Through proper selection of the excitation laser intensity ratio and the corresponding optimal modulation frequency, the modified WM-DPTR glucose measurement mode can be adjusted for maximum sensitivity to the glucose range of interest for accurate evaluation of biologically relevant glucose ranges, from hypoglycemia to hyperglycemia.

In practice, glucose detection instrumentation based on WM-DPTR is able to perform preliminary (coarse) measurements in the maximum dynamic range and relatively low sensitivity mode to locate a patent's glucose concentration range and then use appropriate intensity ratio to switch to the high-resolution mode for precise glucose measurements.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. M. Jones, J. M. Harrison, Diabetes Technol. Ther. 4, 351-359 (2002).
2. Davidson M B. Diabetes Mellitus—Diagnosis and Treatment. 3rd Edition, Churchill Livingstone, New York 1991; 231-32.
3. S. Auxter, Clinical Chemistry News; November, 5-16 (1996).
4. R. McNichols and G. Coté, J. Biomed. Opt. 5, 5-16 (2000).
5. A. Tura, A. Maran, G. Pacini, Diabetes Research and Clinical Practice, 77, 16-40 (2007).
6. "Handbook of Optical Sensing of Glucose in Biological Fluids and Tissues", V. V. Tuchin, Ed., (CRC Press, Boca Raton, Fla., 2008) (first edition).

7. C. J. Pouchert, The Aldrich Library of Infrared Spectra, 3rd. ed., Aldrich Chemical Co. (1981)].
8. H. A. MacKenzie, H. S. Ashton, S. Spiers, Y. Shen, S. S. Freevorn et al. Clin. Chem. 45, 1587-1595 (1999).
9. G. B. Christison, H. A. McKenzie, Med. Biol. Eng. Comput. 31, 284-290 (1993)
10. W. Martin, S. Mirov, R. Venugopalan, Appl. Spec. 59, 881-884 (2005).
11. W. Martin, S. Mirov, R. Venugopalan, J. Biomed. Opt. 7, 613-617 (2002).
12. P. Zheng, C. E. Cramer, C. W. Barnes, J. R. Braig, B. B. Sterling, Diabetes Technology and Therapeutics 2, 1-26. (2000).
13. A. Mandelis, S. Telenkov, "Non-invasive Biothermophotonic Sensor for Blood Glucose Monitoring" U.S. Pat. No. 7,729,734.
14. A. Mandelis, J. Appl. Phys. 78, 647-655 (1995).
15. "Handbook of Chemistry and Physics, R. C. Weast, D. R. Lide, Ed. (CRC Press, Boca Raton, Fla. 1989) (70th edition.)
16. Y. Zhang and S. Tadigadapa, "A novel immunosensing technique based on the thermal properties of biochemicals," Sensors, 2005 IEEE, 41-44 (2005).
17. R. Darros-Barbosa, M. Balaban and A. Teixeira, "Temperature and concentration dependence of heat capacity of model aqueous solutions," Int. J. Food Prop. 6, 239-58 (2003).
18. J. D. Hardy, H. T. Hammel, D. Murgatroyd, J. Appl. Physiol. 9, 257-264 (1956).
19. J. A. Jacques, H. F. Kuppenheim, J. Appl Physiol. 7, 523-528 (1955).
20. F. Tanzer, N. Yazar, H. Yazar, D. Icagasioglu, J. Trop. Pediatrics, 43, 58-60 (1999).
21. L. Rovati, R. R. Ansari, in Handbook of Optical Sensing of Glucose in Biological Fluids and Tissues, V. V. Tuchin, Ed., (CRC Press, Boca Raton, Fla., 2008) (first edition) chap. 16.

Therefore what is claimed is:

1. A method of operating a wavelength modulated differential photothermal radiometry system for detecting the presence of an analyte within a substance, said method comprising the steps of:
providing a first optical beam and a second optical beam, wherein said first optical beam is characterized by a first wavelength and said second optical beam is characterized by a second wavelength, and wherein said first wavelength is selected so that analyte concentrations within a concentration range of interest will cause sufficient absorption of said first optical beam to produce detectable thermal-wave emission, and wherein an absorption coefficient of said analyte at said first wavelength exceeds that at said second wavelength;
producing a first modulated beam and a second modulated beam by modulating an intensity of said first optical beam and an intensity of said second optical beam, respectively; wherein said first modulated beam and said second modulated beam are modulated at a substantially equal modulation frequency, and wherein a phase difference between said first modulated beam and said second modulated beam is approximately 180 degrees;
providing a reference sample substantially free of analyte;
directing and substantially overlapping said first modulated beam and said second modulated beams onto said reference sample;
measuring a first photothermal signal produced by said first modulated beam;
measuring a second photothermal signal produced by said second modulated beam;
obtaining a relative photothermal phase between said first photothermal signal and said second photothermal signal;
controlling a relative intensity of said first modulated beam and said second modulated beam such that a ratio of said first photothermal signal amplitude and said second photothermal signal amplitude is approximately unity; and
controlling a relative phase of said first modulated beam and said second modulated beam so that said relative photothermal phase is approximately 180 degrees.

2. The method according to claim 1, further comprising the steps of:
measuring a differential photothermal signal for one or more standards, each said standard comprising a known analyte concentration, while controlling a relative intensity of said first modulated beam and said second modulated beam to scan a photothermal amplitude ratio of said first photothermal signal and said second photothermal signal near unity; and
selecting said photothermal amplitude ratio corresponding to a desired sensitivity over said concentration range of interest.

3. The method according to claim 2 further comprising the step of generating calibration data for said photothermal amplitude ratio corresponding to said desired sensitivity over said concentration range of interest.

4. The method according to claim 3 further comprising measuring a sample comprising an unknown analyte concentration within said substance, and determining said unknown analyte concentration by relating a differential photothermal signal obtained when measuring said sample to said calibration data.

5. The method according to claim 2 wherein said relative intensity is controlled by varying an intensity of said second modulated beam.

6. The method according to claim 2 wherein said first optical beam is provided by a first laser, and wherein said second modulated beam is provided by a second laser.

7. The method according to claim 6 wherein said photothermal amplitude ratio is controlled by varying a voltage or current of one or more of said first and second lasers.

8. The method according to claim 6 wherein said relative phase is controlled by varying a phase difference between modulation voltages or currents of said first laser and said second laser.

9. The method according to claim 1 further comprising the steps of:
controlling a relative intensity of said first modulated beam and said second modulated beam to scan a relative photothermal amplitude of said first photothermal signal and said second photothermal signal near unity; and
measuring said first photothermal signal and said second photothermal signal; and verifying that said relative photothermal phase is substantially 180 degrees.

10. The method according to claim 1 wherein prior to said step of controlling said relative phase, an intensity of said first modulated beam is controlled so that an amplitude of first photothermal signal is approximately half of a full-scale amplitude range corresponding to said concentration range of interest.

11. The method according to claim 1 wherein said substance is tissue and said analyte is glucose.

12. The method according to claim 1 further comprising the step of:

measuring a differential photothermal signal for one or more standards, each said standard comprising a known analyte concentration, while controlling a relative intensity of said first modulated beam and said second modulated beam to scan a relative photothermal amplitude of said first photothermal signal and said second photothermal signal near unity; and determining calibration data based on a relationship between each known analyte concentration and a relative intensity at which a phase flip-over occurs.

13. The method according to claim 12 further comprising measuring a sample comprising an unknown analyte concentration within said substance, and determining said unknown analyte concentration by relating a relative intensity at which phase flip-over occurs when measuring said sample to said calibration data.

14. A method of operating a wavelength modulated differential photothermal radiometry system for detecting the presence of an analyte within a substance, said method comprising the steps of:

providing a first optical beam and a second optical beam, wherein said first optical beam is characterized by a first wavelength and said second optical beam is characterized by a second wavelength, and wherein said first wavelength is selected so that analyte concentrations within a concentration range of interest will cause sufficient absorption of said first optical beam to produce detectable thermal-wave emission, and wherein an absorption coefficient of said analyte at said first wavelength exceeds that at said second wavelength;

producing a first modulated beam and a second modulated beam by modulating an intensity of said first optical beam and an intensity of said second optical beam, respectively;

wherein said first modulated beam and said second modulated beam are modulated at a substantially equal modulation frequency, and wherein a phase difference between said first modulated beam and said second modulated beam is approximately 180 degrees;

providing a reference sample comprising a known concentration of analyte;

directing and substantially overlapping said first modulated beam and said second modulated beams onto said reference sample;

obtaining a differential photothermal signal by detecting emission radiated by said reference sample with a phase-sensitive detection system; and varying an intensity ratio of said first modulated beam and said second modulated beam to minimize said differential photothermal signal.

15. The method according to claim 14 wherein said known concentration of analyte is approximately zero.

16. The method according to claim 14 wherein said substance is tissue and said analyte is glucose.

17. The method according to claim 14 further comprising obtaining calibration data by relating signals obtained from standard samples with known analyte concentrations to said known analyte concentrations.

18. The method according to claim 17 further comprising measuring a sample comprising an unknown analyte concentration within said substance, and determining said unknown analyte concentration by relating a differential photothermal signal obtained when measuring said sample to said calibration data.

19. The method according to claim 14 wherein said intensity ratio is varied by controlling one or more of a spatial overlap and a relative spatial size of said first modulated beam and said second modulated beam.

20. The method according to claim 19 wherein said intensity ratio is varied by controlling a diameter of an iris placed in a path of one of said first modulated beam and said second modulated beam.

21. The method according to claim 14 wherein said step of obtaining a signal by detecting emission radiated by said reference sample with a phase-sensitive detection system comprises the steps of:

collecting said emission radiated by said reference sample;

directing said emission onto a detector, wherein said detector is adapted to produce a signal related to said emission;

providing said signal and a reference signal to a lock-in amplifier; and obtaining a phase-sensitive differential photothermal signal.

22. The method according to claim 21 further comprising the step of spectrally filtering any collected photothermal radiation having a wavelength corresponding to said first modulated beam and said second modulated beam.

23. A method of operating a wavelength modulated differential photothermal radiometry system for detecting the presence of an analyte within a substance, said method comprising the steps of:

a) providing a first optical beam and a second optical beam, wherein said first optical beam is characterized by a first wavelength and said second optical beam is characterized by a second wavelength, and wherein said first wavelength is selected so that analyte concentrations within a concentration range of interest will cause sufficient absorption of said first optical beam to produce detectable thermal-wave emission, and wherein an absorption coefficient of said analyte at said first wavelength exceeds that at said second wavelength;

b) producing a first modulated beam and a second modulated beam by modulating an intensity of said first optical beam and an intensity of said second optical beam, respectively; wherein said first modulated beam and said second modulated beam are modulated at a substantially equal modulation frequency, and wherein a phase difference between said first modulated beam and said second modulated beam is approximately 180 degrees;

c) selecting an intensity ratio of said first modulated beam and said second modulated beam;

d) providing a reference sample comprising a known concentration of analyte;

e) directing and substantially overlapping said first modulated beam and said second modulated beams onto said reference sample;

f) obtaining a differential photothermal signal by detecting emission radiated by said reference sample with a phase-sensitive detection system;

g) repeating steps d) to f) one or more times to measure differential photothermal signals for one or more additional standard samples, wherein each said additional standard samples comprise different known analyte concentrations;

h) obtaining a calibration curve by relating said differential photothermal signals to said known analyte concentrations;

i) repeating steps c) to h) to obtain an additional calibration curve corresponding to a different intensity ratio; and j) selecting a preferred calibration curve having a desired sensitivity over a predetermined range of analyte concentration, and placing said system into a configuration corresponding to said preferred calibration curve.

24. The method according to claim 23 further comprising repeating step i) one or more times prior to performing step j).

25. The method according to claim 23 wherein said substance is tissue and said analyte is glucose.

26. The method according to claim 23 further comprising measuring a sample comprising an unknown analyte concentration within said substance, and determining said unknown analyte concentration by relating a signal obtained when measuring said sample to said preferred calibration curve.

* * * * *